United States Patent [19]

Saksena et al.

[11] Patent Number: 5,039,676
[45] Date of Patent: Aug. 13, 1991

[54] TRI- AND TETRA-SUBSTITUTED-OXETANES AND TETRAHYDROFURANS AND INTERMEDIATES THEREOF

[75] Inventors: Anil K. Saksena, Upper Montclair; Viyyoor M. Girijavallabhan, Parsipanny; Ashit K. Ganguly, Upper Montclair; Dinanath F. Rane, Morganville, all of N.J.

[73] Assignee: Schering Corporation, Kenilworth, N.J.

[21] Appl. No.: 460,342

[22] Filed: May 11, 1990

[51] Int. Cl.$^5$ .................. A61K 31/495; C07D 407/14
[52] U.S. Cl. .................... 514/254; 514/252; 514/253; 544/262; 544/364; 544/366; 544/369; 544/370
[58] Field of Search ............... 544/262, 364, 366, 369, 544/370; 514/252, 253, 254

[56] References Cited

U.S. PATENT DOCUMENTS

| | | | |
|---|---|---|---|
| 4,518,415 | 5/1985 | Marchington et al. | 514/383 |
| 4,618,616 | 10/1986 | Richardson et al. | 514/383 |
| 4,634,466 | 1/1987 | Noon et al. | 514/383 |
| 4,636,247 | 1/1987 | Clouph et al. | 514/383 |

FOREIGN PATENT DOCUMENTS

| | | |
|---|---|---|
| 151084 | 8/1985 | European Pat. Off. . |
| 243983 | 11/1987 | European Pat. Off. . |
| 2597868 | 3/1987 | France . |

OTHER PUBLICATIONS

Greiner et al., Chem Abst. vol. 108-217777s (1988).

*Primary Examiner*—Cecilia Shen
*Attorney, Agent, or Firm*—Thomas D. Hoffman; Edward H. Mazer; Gerald S. Rosen

[57] ABSTRACT

This invention relates to tri- and tetra-substituted-oxetanes, e.g. (±)-cis- and (±)-trans-2-[(4-(4-isopropylpiperazin-1-yl)phenoxy)methyl]-4-(2,4-dihalophenyl)-4-[1H-1,2,4-triazol-1-yl)-methyl]oxetane and tri- and tetra-substituted-tetrahydrofurans, e.g. (±)-cis- and (±)-trans-1-[4-[[2-(2,4-dihalophenyl)tetrahydro-2-[(1H-azol-1-yl)methyl]-5-furanylmethoxy]phenyl]-4-yl-1-substituted piperazine-3-one and related derivatives which exhibit antifungal and antiallergy activities, pharmaceutical composition thereof, methods of their use in treating or preventing susceptible fungal infections and allergic reactions in a host including warm-blooded animals such as humans.

12 Claims, No Drawings

5,039,676

TRI- AND TETRA-SUBSTITUTED-OXETANES AND TETRAHYDROFURANS AND INTERMEDIATES THEREOF

BACKGROUND OF THE INVENTION

This invention relates to tri- and tetra-substituted-oxetanes, e.g. (±)-cis- and (±)-trans-2-[(4-(4-isopropyl-piperazin-1-yl)phenoxy)methyl]-4-(2,4-dihalophenyl)-4-[1H-1,2,4-triazol-1-yl)methyl]oxetane and tri- and tetra-substituted-tetrahydrofurans, e.g. (±)-cis-and (±)-trans-1-[4-[[2-(2,4-dihalophenyl)tetrahydro-2-[*1H-azol-1-yl)methyl]-5-furanyl]methoxy]phenyl]-4-yl-1-substituted piperazine-3-one and related derivatives which exhibit, e.g. antifungal, antiallergy as well as immunomodulating activities, pharmaceutical compositions thereof, methods of their use in treating or preventing susceptible fungal infections, hyperproliferative skin disease and allergic reactions as well as treating autoimmune diseases in a host including warm-blooded animals such as humans.

This invention also relates to antifungally active intermediates and to intermediates for preparation of the antifungal, antiallergic and immunomodulating compounds.

U.S. Pat. Nos. 4,518,415 and 4,636,247 disclose 1-(tetrahydrofurylmethyl)azoles useful as plant growth regulators and fungicides which are disubstituted at the 2-position by imidazol-1-ylmethyl or triazol-1-ylmethyl and phenyl or substituted phenyl and at 3, 4 and 5-positions by hydrogen and substituted alkyl, cyloalkyl, aralkyl, or phenyl. However, these references do not disclose the compounds of the present invention.

SUMMARY OF THE INVENTION

The present invention provides compounds represented by the formula I:

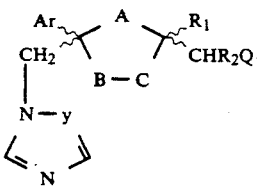

wherein;

Ar is thienyl, pyridyl, biphenyl, phenyl or phenyl substituted by one or more of halo, nitro, cyano, lower alkyl, lower alkoxy or perhalo(lower)alkyl;

Y is CH or N;

either one of A, B and C is Oxygen and the remaining two of A, B and C are $CH_2$ or A is Oxygen, B is $CH_2$ and C is a direct bond;

Q is 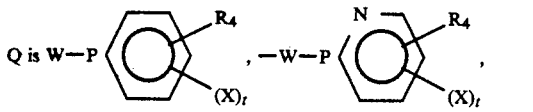

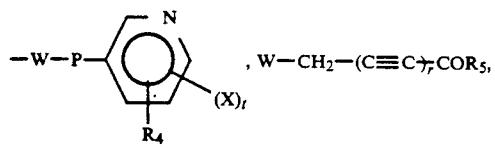

$-W-CH_2-(C{\equiv}C)_r Ar$, $W-CH_2-(C{\equiv}C)_r-C(R_{10})_t$, $-W-CH_2-CH{=}CH-C{\equiv}C-(R_{10})_t$, $W-CH_2-(C{\equiv}C)_r-CH_2-NR_6R_7$, $-W-CH(R_8)-(CH_2)_p-CO_2R_9$, OH, $-O-\overset{\overset{O}{\|}}{C}-NR_{13}R_9$ or $-N-R_{14}R_9$ W is $-NR_5-$, $-O-$ or $-S(O)_n-$;

X is $NO_2$, $-P-NR_6R_7$,

Ar, $OR_3$ or halogen;

P is a direct bond, $-CHR_{11}-$ or $-CHR_{11}CHR_{12}-$;

$R_1$, $R_8$, $R_9$ and $R_{10}$ are independently hydrogen, lower alkyl or lower alkyl substituted by one or more hydroxy groups;

$R_2$, $R_4$, $R_{11}$, $R_{12}$ and $R_{14}$ are hydrogen, hydroxy, lower alkyl or lower alkyl substituted by one or more hydroxy groups;

$R_3$ and $R_{13}$ are independently hydrogen, lower alkyl, ($C_2$-$C_8$) perhaloalkanoyl or ($C_2$-$C_8$) alkanoyl;

$R_6$ and $R_7$ are independently hydrogen, lower alkyl, phenyl or phenyl substituted by one or more of halo, perhalo(lower)alkyl, ($C_2$-$C_8$)alkanoyl, lower alkyl, lower alkyl substituted by one or more hydroxy groups, lower alkoxy, or 2-(lower)alkyl-3-oxo-1,2,4-triazol-4-yl, or $R_6$ and $R_7$ taken together with the nitrogen atom in $NR_6R_7$ form unsubstituted or substituted five or six member heterocyclyl ring systems containing carbon and one to four heteroatoms chosen from N, O and S, said heterocyclyl substituents being ($C_1$-$C_8$)alkanoyl, lower alkyl, lower alkoxycarbonyl, aminocarbonyl, N-lower alkylaminocarbonyl, N,N-di(lower alkyl)amino carbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkylamino, N,N-di(-lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, or

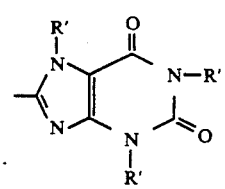

R' = Lower Alkyl phenyl or phenyl substituted by one or more of halo, perhalo lower alkyl, ($C_2$-$C_8$) alkanoyl, lower alkyl, lower alkyl substituted by one or more hydroxy group, lower alkoxy, 1H,2,4-triazol-1-yl or 2-lower alkyl-3-oxo-1,2,4-triazol-4-yl;

$R_5$ is a lower alkyl, lower alkoxy, amino, N,N-dilower alkylamino, phenyl or phenyl substituted by one or more of halo, perhalo lower alkyl, lower alkoxy, nitro, cyano, (C$_2$-C$_8$)alkanoyl;

p is 0, 1, 2, 3, 4 or 5;

n is 0, 1 or 2;

r is 1 or 2; and t is 0, 1, 2 or 3;

and the stereochemical isomers thereof in racemic or optically active form;

or a pharmaceutically acceptable salt thereof;

with the proviso that when R$_2$ or R$_{11}$ or R$_{12}$ is attached to a carbon atom adjacent to —NR$_5$, —S(O)$_n$ or —O—, R$_2$ or R$_{11}$ or R$_{12}$ is not hydroxy.

The present invention also provides a compound represented by formula II:

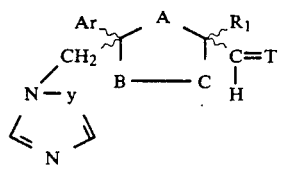

wherein Ar is as defined hereinabove and one of A, B or C is Oxygen and the remaining two of A, B or C are —CH$_2$—;

T is =O, =NOR$_1$, =NNR$_1$R$_2$ or $$=NNR_1\overset{O}{\underset{\|}{C}}-N(R_1R_2);$$

R$_1$ is hydrogen, lower alkyl or lower alkyl substituted by one or more hydroxy groups; and R$_2$ is hydrogen, hydroxy, lower alkyl or lower alkyl substituted by one or more hydroxy groups.

The compounds represented by formula II are intermediates for the preparation of the tetrahydrofuran compounds represented by formula I.

The present invention also provides a compound represented by formula IIa

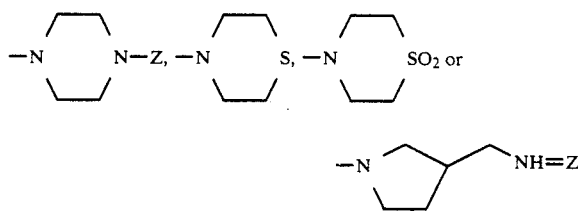

wherein Y, Ar, R$_1$, R$_2$, R$_6$ and R$_7$ are as previously defined and either one of A, B and C is Oxygen and the remaining two of A, B and C are CH$_2$ or A is Oxygen and B is CH$_2$ and C is a direct bond;

Preferred compounds of formula IIa include those wherein NR$_6$R$_7$ form unsubstituted or substituted five or six member heterocyclyl ring systems containing carbon and one to four heteroatoms chosen from N, O and S, said heterocyclyl substituents being (C$_1$-C$_8$) alkanoyl, lower alkyl, lower alkoxycarbonyl, aminocarbonyl, N-lower alkylaminocarbonyl, N,N-di(lower alkyl)aminocarbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkyl-amino, N,N-di(lower alkyl)amino, 1,3-imidazol-1-yl, 2-loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, or

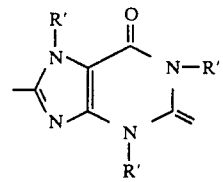

R' = Lower alkyl phenyl or phenyl substituted by one or more of halo, perhalo lower alkyl, (C$_2$-C$_8$)alkanoyl, lower alkyl, lower alkyl substituted by one or more hydroxy groups, lower alkoxy, 1H,2,4-triazol-1-yl or 2-lower alkyl-3-oxo-1,2,4-triazol-4-yl; R$_5$ is a lower alkyl, lower alkoxy, amino, N,N-dilower alkylamino, phenyl or phenyl substituted by one or more of halo, perhalo lower alkyl, lower alkoxy, nitro, cyano, (C$_2$-C$_8$)alkanoyl.

The more preferred compounds of formula IIa are compounds wherein NR$_6$R$_7$ is

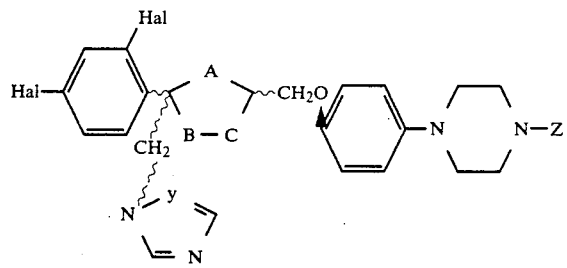

and Z is a hydrogen, (C$_1$-C$_8$) alkanoyl, lower alkyl, (C$_1$-C$_8$) perhaloalkanoyl or phenyl substituted by 2-loweralkyl-3-oxo-1,2,4-triazol-4-yl.

Particularly preferred compounds of formula I represented by the formula

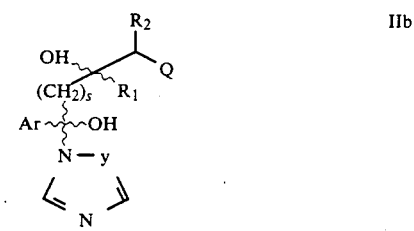

wherein:

one of A, B and C is oxygen and the remaining two of A, B and C are —CH$_2$—; two of A, B and C are —CH$_2$—;

Hal is Cl or F;

Z is lower alkyl, (C$_2$-C$_8$)alkonoyl, or phenyl substituted by 2-loweralkyl-3-oxo-1,2,4triazol-4-yl.

The present invention also is directed at a compound of the formula

IIb wherein Ar, $R_1$, $R_2$, Q and y are as defined in claim 1 and s is 1 or 2.

The compounds of formulas I, IIa, and IIb may be formulated into pharmaceutical compositions with a pharmaceutically acceptable carrier or diluent. The compounds of formula I may be used to treat mammals suffering from susceptible fungal infections, hyperproliferative skin disease (such as psoriasis), allergic reactions and/or inflammation as well as autoimmune reactions and diseases and immunological diseases by administering an effective amount for such purpose to the mammal.

The invention provides a method for treating hyperproliferative skin disease in a host which comprises administering to such a host, e.g. a warm-blooded animal such as man in need of such treating an hyperproliferatively effective amount of a compound represented by the formula I and a pharmaceutically acceptable carrier or diluent.

The invention also provides a method of treating or preventing susceptible fungal infections which comprises administering to a host in need of such treating or preventing an antifungally effective amount of a compound of formula I, formula IIb or a pharmaceutical composition comprising such a compound and a pharmaceutically acceptable carrier or diluent.

The present invention still further provides a method of treating or preventing an allergic reaction in a host which comprises administering to such a host, e.g., warm-blooded animals including humans in ned of such treatment or prevention, an antiallergically effective amount of a compound represented by formula I, or a pharmaceutical composition thereof.

The invention provides a method of treating autoimmune reactions and diseases and immunological diseases including skin graft rejection, bone marrow rejection and organ transplant rejection phenomena which comprises administering to a host in need of such treating an effective amount of a compound of formula IIa or a pharmaceutical composition comprising such a compound and a pharmaceutically acceptable carrier or diluent.

The present invention also is directed at a method of preparing a compound of formula I I. Wherein one of A, B and C is oxygen and the two remaining A, B and C are —$CH_2$— a) reacting a compound of the formula

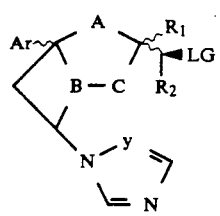

where LG is a leaving group, with $Q^-$ to produce a compound of the formula

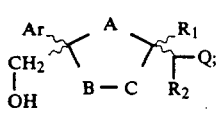

b) converting the free hydroxy group of the product of step a) into a leaving group LG to produce a compound of the formula

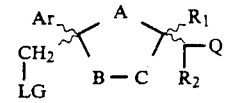

and reacting the so-formed compound with an azole anion to produce a compound of the formula

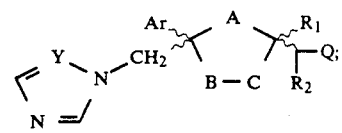

II. where A is oxygen, B is $CH_2$ and C is $CH_2$ reacting a compound of the formula

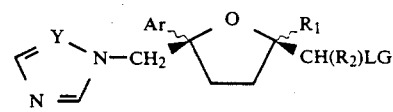

with $Q^-$ to produce

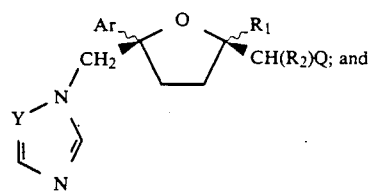

and III. where A is oxygen, B is —$CH_2$ and C is a direct bond reacting a compound of the formula

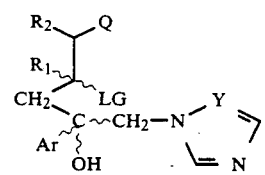

with a strong base to produce a compound of the formula

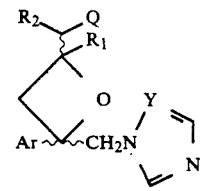

DETAILED DESCRIPTION OF THE INVENTION AND THE PREFERRED EMBODIMENTS

As used in the specification and claims, the term "halo" means bromine, chlorine or fluorine with chlorine and fluorine being preferred, fluorine is most preferred.

The term "lower alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso-, tert-hexyl and the like.

The term "perhaloloweralkyl" refers to "lower alkyl" groups having only halogen substituents replacing all the hydrogens on the carbons, e.g., —CCl$_2$—CF$_3$, —CF$_2$—Cl$_3$ as well as perhalo groups such as —CF$_2$—CF$_3$ or —CF$_3$; trifluoromethyl is preferred.

The term "(C$_2$-C$_8$)alkanoyl" refers to straight and branched chain alkanoyl groups having 2 to 8 carbon atoms such as acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. Acetyl is preferred.

The term "(C$_2$-C$_8$)perhaloalkanoyl" refers to (C$_2$-C$_8$)alkanoyl groups as defined hereinabove wherein the alkanoyl groups have only halogen substituents replacing the hydrogens on the alkane chain, e.g. perhaloacetyl, perhalopropanoyl and the like. Perchloro- and perfluoroacetyl are preferred.

The term "(C$_1$-C$_8$)alkanoyl" includes a formyl and "(C$_2$-C$_8$)alkanoyl" which is defined hereinabove.

The term "lower alkoxy" means a lower alyl moiety univalently bonded to divalent oxygen, —O— and includes methoxy, ethoxy, n- and iso-propoxy, n-, sec- and tert-butoxy and the like.

The term "lower alkoxy carbonyl" means the group R'

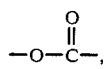

wherein R' is lower alkyl.

The term "aminocarbonyl" means the group

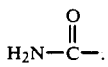

The terms "N-lower alkylaminocarbonyl" and "N,N-lower alkylaminocarbonyl" mean the groups

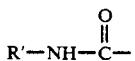

and

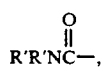

respectively, wherein R' is lower alkyl.

The term "aminothiocarbonyl" means the group

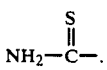

The terms "N-lower alkylaminocarbonyl" and N,N-lower alkylaminocarbonyl" mean the groups

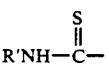

and

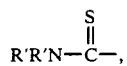

wherein R' is lower alkyl.

The term "lower alkylsulfonyl" means the group R'—SO$_2$—, wherein R' is lower alkyl.

The term "phenyl-substituted lower alkyl sulfonyl" means the group C$_6$H$_5$—R'—SO$_2$, wherein R' is lower alkyl.

The terms "N-lower alkylamino" and "N,N-dilower alkylamino" mean the groups R'NH- and R'R'N-, respectively, wherein R' is lower alkyl.

The term "2-lower alkylsulfenyl-1,3-imidazol-1-yl" means the group having the formula

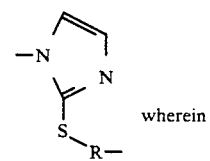 wherein wherein R' is loweralkyl.

The term "1-lower alkylbenzimidazol-2-yl" means the group

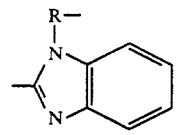

wherein R' is lower alkyl.

The term "2-lower alkyl-3-oxo-1,2,4-triazol-4-yl" means a moiety represented by the formula

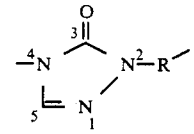

wherein R' is "lower alkyl" as defined hereinabove.

The term "heterocyclyl" refers to five and six-membered ring systems containing at least one carbon and one to four heteroatoms chosen from N, O and S, SO and SO$_2$. Typical suitable heterocyclyls include morpholino, thiomorpholino, 4-oxothiomopholino, 4,4-dioxothiomorpholino piperazino, pyrrolidino, piperidino, imidazolyl, 1,2,4-triazolyl, furanyl, thienyl, thiadiazolyls, especially 1,2,3-thiadiazol-4-yl, and 1,2,3-thiadiazol-5-yl, and pyridyls. The heterocyclyl may be attached via a carbon atom, e.g., N-methylpiperidin-4-yl, N-methylmorpholin-2-yl or via the nitrogen atom, e.g., piperidin-1-yl (commonly called piperidino), morpholin-4-yl (commonly called morpholino), N-methylpiperazin-4-yl (commonly called N-methylpiperazino), 1H-1-imidazol-1-yl or 4H-1,2,4-triazol-4yl and piperazino are the preferred heterocyclyls.

Substituted heterocyclyls include lower alkyl substituted heterocyclyls, especially N-loweralkylheterocyclyls such as N-methylmorpholin-4-yl, N-ethylpiperazino, N-(1-methylethyl)piperazino, but also 2-methylpyrrolidino, 4-methylpiperidino, 5-methyl-1H-1,2,4-triazol-3-yl, 3-methyl-1-phenyl-1H-1,2,4-triazol-5-yl, and 2-methylpyridyl; (C$_2$-C$_8$)alkanoyl heterocyclyls such as 2-acetylthiophenyl, 2-acetylpyrrolidino; haloheterocyclys such as 2-halo-3-thienyl, 2,5-dihalo-3-thienyl, and 5-halo-2-thienyl; N-($C_2$-$C_8$)alkanoyl heterocyclyls such as N-acetylpiperazino and 4-acetylpiperidino; and aryl substituted heterocyclyls include heterocyclyls substituted by phenyl or substituted phenyl as defined herein such as N-phenylpiperazino, N-(4-chlorophenyl)-piperazino, 2-(4-trifluoromethylphenyl)piperazino, and N-(p-toluyl)piperazino, N-(4-methoxyphenyl)piperazino. Piperazino is the preferred substituted heterocyclyl.

Compounds of the present invention represented by formula I can exist in two isomeric forms, cis and trans. With reference to formulas I and II and IIa "cis" means Ar and $R_1$ are on the same side of the plane defined by the 4- or 5-membered ring. With reference to formula I, the cis- and trans-series of the 5-membered ring, compounds are shown by the formulas hereinbelow:

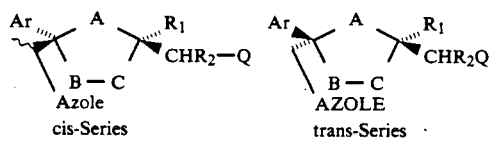

| Type i: | A is Oxygen, and |
| --- | --- |
|  | B and C are each —$CH_2$— |
| Type ii: | B is Oxygen, and |
|  | A and C are each —$CH_2$— |
| Type iii: | C is Oxygen, and |
|  | A and B are each —$CH_2$— |
| Type iv: | A is Oxygen, |
|  | B is —$CH_2$—, and |
|  | C is a direct bond. |

The cis-series is preferred for Types i, ii, iii and iv.

Examples of the preferred cis-series for compounds of this invention are shown by the formulas hereinbelow:

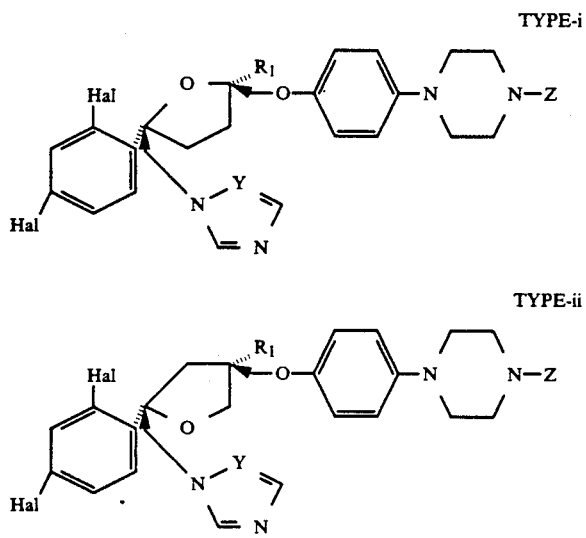

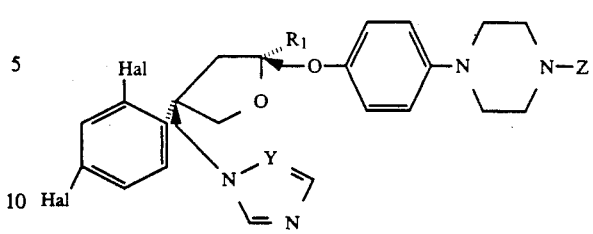

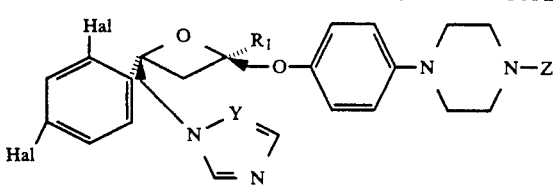

Wherein Hal is F or Cl, preferably F; $R_1$ is hydrogen and is lower alkyl, ($C_2$-$C_8$)alkanoyl or phenyl substituted by 2-loweralkyl-3-oxo-1,2,4-triazol-4-yl.

In the formula labelled Type i "cis-2,5", the $R_1$ group and the 2,4-dichlorophenyl group are both positioned on the same side or face or plane (below) of the formula. In the "trans-2,5" formula (not shown), the groups are positioned on opposite faces of the formula. Both cis and trans forms of Types i, ii, iii and iv are contemplated as being within the scope of this invention as are individual optical isomers e.g., ($\pm$)-cis-2,5 and ($\pm$)-cis-2,5, each of which can be obtained by resolution of a racemic mixture [($\pm$)-cis-2,5] by conventional means well known to those skilled in the art. Compounds of formula II may also be resolvable, i.e., exist as individual optical isomers or mixtures thereof.

Compounds represented by formula I exhibit broad spectrum antifungal activity, in conventional antifungal screening tests, against human and animal pathogens, such as the following: *Aspergillus, Candida, Epidemophyton, Geotrichum, Monosporium, Rhodotorula, Saccharomyces, Torulopsis* and *Trichophyton*.

The compounds of formula I exhibit topical and oral fungal activity in in vivo tests in animals that is comparable to or better than that for ketoconazole, a commercial product.

The present invention also provides a composition for treating or preventing fungal infections comprising an antifungally effective amount of a compound represented by formula I or a pharmaceutically acceptable salt thereof and a pharmaceutically acceptable carrier or diluent.

The preferred pharmaceutically acceptable salts are nontoxic acid addition salts forms by adding to the compounds of the present invention about a stoichiometric amount of a mineral acid, such as HCl, HBr, $H_2SO_4$ or $H_3PO_4$, or of an organic acid, such as acetic, propionic, valeric, oleic, palmitic, stearic, lauric, benzoic, lactic, para-toluene sulfonic, methane sulfonic, citric, maleic, fumaric, succinic and the like.

The pharmaceutical compositions of the present invention may be adapted for oral, parenteral, topical or vaginal administration. They are formulated by combining the compound of formula I or an equivalent amount of a pharmaceutically acceptable salt I with any suitable, inert, pharmaceutically acceptable carrier or diluent.

Examples of suitable compositions include solid or liquid compositions for oral administration such as tablets, capsules, pills, powders, granules, solutions, suppositories, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired.

Topical dosage forms may be prepared according to procedures well known in the art, and may contain a variety of ingredients, excipients and additives. The formulations for topical use include ointments, creams, lotions, powders, aerosols, pessaries and sprays.

For preparing suppositories, a low melting wax such as a mixture of fatty acid glycerides or cocoa butter is first melted, and the active ingredients is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parenteral administration. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof.

Parenteral forms to be injected intravenously, intramuscularly, or subcutaneously are usually in the form of a sterile solution, and may contain salts or glucose to make the solution isotonic.

The topical dosage for humans for antifungal use in the form of pharmaceutical formulation comprising a compound of formula I (usually in the concentration in the range from about 0.5% to about 20% preferably from about 1% to about 10% by weight) together with a non-toxic, pharmaceutically acceptable topical carrier, is applied several times daily to the affected skin until the condition has improved.

In general, the oral dosage for humans for antifungal use ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans for antifungal use ranges from about 0.5 mg per kilogram of body weight per day to about 20 mg per kilogram of body weight per day, in single or divided doses, with about 10 mg per kilogram of body weight per day being preferred.

The compounds of this invention also are useful in treating or preventing an allergic reaction and/or inflammation in a host e.g. a warm blooded mammal such as man.

The pharmaceutical compositions useful for treating or preventing allergic reactions and/or inflammation are analogous to those described hereinabove in reference to the antifungal pharmaceutical composition.

The compounds of formula I are effective non-adrenergic, non-antichlolinergic, anti-anaphylactic agents. The compounds may be administered by any convenient mode of administration for treatment of allergic reactions employing an antiallergically, or antiinflammatory effective amount of a compound of formula I for such mode.

In general, the oral dosage for humans for antiallergy and/or antiinflammatory use ranges from about 10 mg to about 500 mg per kilogram of body weight per day, in single or divided doses. Preferably the total daily dosage is administered in 2-4 divided doses per day.

In general, the parenteral e.g. intravenous dosage for humans from antiallergy and/or antiinflammatory use ranges from about 0.1 mg per day to about 10 mg per kilogram of body weight per day, in single or divided doses.

The compounds of formula I also may be administered by inhalation (aerosol or nebulizer). In general, the inhalation dosage for humans for antiallergy use ranges from about 0.1 to 5 mg per puff. One to four puffs may be taken every 4 hours.

When administered for the treatment of hyperproliferative skin disease, e.g. psoriasis, a compound of formula I may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at daily doses ranging from about 0.1 mg/kg of body weight to about 500 mg/kg of body weight, preferably in doses of 10 mg to 100 mg/kg of body weight, which may be administered in single or divided doses. When administered rectally, the compounds of formula I may be administered in doses ranging from about 0.1 mg to about 1000 mg. When administered parenterally, the compounds of formula I are effective for the treatment of hyperproliferative skin disease in daily doses ranging from about 0.1 mg/kg body weight to about 10 mg/kg body weight which may be administered in single or divided doses.

Included within the invention are preparations for topical application to the skin whereby the compounds having structural formula I are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising a compound of formula I, (usually in concentrations in the range of from about 0.01 percent to about 10 percent, preferably from about 1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

The compounds represented by formula IIa exhibit in vitro immunomodulating activity in a conventional screening test detailed hereinbelow.

The compounds of formula IIa are useful as immunosuppressives as indicated by their inhibition of the proliferation of T cells and B cells and are therefore useful in treating autoimmune disease and reaction and other immunological diseases including bone marrow rejection, organ transplant rejection as well as skin graft rejection phenomena in a host, e.g. a warm blooded mammal such as man.

The pharmaceutical compositions useful for treating autoimmune diseases and reactions in man are analogous to those described hereinabove with reference to the antifungal pharmaceutical composition for compounds of formula I.

The compounds of formula IIa may be administered by any convenient mode of administration for treatment of autoimmune diseases, reactions and other immunological diseases by employing an immunomodulating effective amount of a compound of formula IIa for such mode.

The topical dosage for humans for immuno-modulating use in the form of a pharmaceutical formulation comprising a compound of formula IIa (usually in the concentration in the range from about 0.1% to about 5%, preferably from about 1% to about 3% by weight) together with a non-toxic, pharmaceutically acceptable topical carrier, is applied several times daily to the affected skin until the condition has improved.

In general, the oral dosage for humans for immunomodulating use ranges from about 1 mg per kilogram of body weight to about 300 mg per kilogram of body weight per day, in single or divided doses, with about 50 mg per kilogram of body weight to about 200 mg per kilogram of body weight per day being preferred.

In general, the parenteral dosage for humans for immunomodulating use ranges for about 25 mg per kilogram of body weight per day to about 300 mg per kilogram of body weight per day, in single or divided doses, with about 50 to about 100 mg per kilogram of body weight per day being preferred.

It will be appreciated that the actual preferred dosages of the compounds of the present invention of formulas I or IIa or pharmaceutically acceptable salts thereof will vary according to the particular composition formulated, the mode of application and the particular situs, host, the allergic reaction or disease being treated. Many factors that modify the action of the drug will be taken into account by the attending clinician when determining a treatment regimen, e.g., age, body weight, sex, diet, time of administration, rate of excretion, condition of the host, drug combinations, reaction sensitivities and severity of the disease or symptoms of the allergic and/or inflammatory reaction. Administration can be carried out continuously or periodically within the maximum tolerated dose. Optimal application rates for a given set of conditions can be readily ascertained by the attending clinician using conventional dosage determination tests.

As a result of the administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

The anti-allergy property of the compounds of formula I is evaluated by measuring the inhibition of the release of the mediator SRS-A (slow reacting substance of anaphylaxis) from sensitized guinea pig lung fragments after antigen challenge. The test procedure utilized is described hereinbelow.

MEASUREMENT OF SRS-A RELEASE FROM SENSITIZED GUINEA PIG LUNGS

(a) Sensitization of Animals

The release of SRS-A and histamine was studied in lungs from actively sensitized guinea pigs. Male Harley guinea pigs (250–300 g, obtained from Charles River or Dutchland Farms) were sensitized with 5 mg ovalbumin injected intraperitoneally and 5 mg subcutaneously in 1 ml saline on day one, and 5 mg ovalbumin injected intraperitoneally on day four. The sensitized animals were used 3–4 weeks later.

(b) Release of SRS-A

Sensitized guinea pigs were killed by a flow to the head and the lungs removed and cleaned of visable connective tissue, trachea and large blood vessels. The lungs from individual animals were sliced into fragments approximately 1 mm in thickness using a McIlwain chopper and then washed with oxygenated Tyrode's buffer. Weighed aliquots (approximately 400 mg wet weight) of lung were transferred into vials containing 2 ml of fresh Tyrode's solution and incubated in the presence or absence of test compound 12 min at 37° C. followed by challenge of the tissue with 20 μg ovalbumin/ml (final concentration). After an additional 15 min incubation, the vials were cooled to 4° C. and 1.5 ml of clear supernatant media was removed and mixed with 6 ml of cold 100% ethanol. This mixture was thoroughly vortexed and kept at −15° C. for 30 min to allow precipitation of protein. The samples were then centrifuged at 1000 x g for 15 min at 2° C. and the clear supernatant fluid removed into polyethylene tubes and taken to dryness at 50° C. under a stream of $N_2$ gas. The samples were stored at −70° C. until assayed for SRS-A by bioassay or radioimmune assay.

The compounds of formula I inhibit the release of SRS-A from sensitized guinea pig lung fragments as measured using the test techniques described above.

The compounds of formula I inhibit 5-lipoxygenase activity, which inhibitory activity has been associated with anti-allergy and anti-inflammatory activity. The compounds of formula I are thus useful for the treatment of allergies, allergic chronic obstructive lung diseases, inflammation, arthritis, bursitis, tendonitis, gout and other inflammatory conditions. The 5-lipoxygenase inhibitory activity of the compounds of formula I may be demonstrated by the procedure described below:

5-Lipoxygenase and Cyclooxygenase Assays with MC-9 Mast Cells

The IL-3-dependent murine mast cell clone, MC-9, was used to test the effects of compounds of formula I on cyclooxygenase and lipoxygenase activities. The MC-9 cell line was grown in suspension culture (0.4 to $1.2 \times 10^6$ cells/ml) in RPMI 1640 medium (Gibco) with 10% fetal bovine serum (hyclone) and 2–5% conconavalin-A conditioned supernatant [Musch et. al., Protagandins, (1985) pp 405–430, ]. Cells were harvested, washed twice by centrifugation, and resuspended in a $Ca^{++}$-free HEPES buffer (25 mM HEPES, 125 mM NaCl, 2.5 mM KCl, 0.7 mM $MgCl_2$, 0.5 mM EGTA and 10 mM glucose at pH 7.4).

MC-9 cells (0.39 ml at $7.5 \times 10^6$ cells/ml) were preincubated with DMSO vehicle with or without test compound (1 μl) for 4 minutes ("min") then incubated 5 min with [$^{14}$C] arachidonic acid (Amersham, 59 Ci/mole) at a 9 μm final concentration and A23187 (Calbiochem) at a 1 μM final concentration added in 10 μl of water:ethanol (9:1). The reaction was stopped by addition of methanol (0.4 ml), and cellular debris was removed by centrifugation. Aliquots (250 μl) of the incubations were run on a Waters two pump HPLC system fitted with a Waters C18, 10 μ 8×100 mm μ-Bondapak radial compression column and C18 "Guard Pak". The column was initially eluted at 3 ml/min with water:methanol:acetic acid (67:33:0.08) containing 1 mM EDTA adjusted to pH 6.0 with ammonium hydroxide (Pump A). At 4 min, a linear gradient to reach 100% methanol (Pump B) at 9 min was established. Between 13 and 14 min, methanol was exchanged for the initial eluting solvent and by 19 min the column had been reequilibrated for the next sample. The effluent was analyzed by a continuous flow radioactivity monitor (model ROMONA-D) interfaced with a Hewlett Packard Lab Automation System for quantitation of radioactive products. These were predominantly prostaglandin $D_2$ which eluted at 4 in ($PGD_2$), leukotriene $C_4$ ($LTC_4$) which eluted at 6 min, and 5-hydroxyeicosatetraenoic acid (5-HETE) which eluted at 11 min (Musch, et al. (1985) Prostagandins 29, 405-430).

The results with and without test compounds were used to calculate percent inhibition of $PGD_2$, $LTC_4$ and HETE production for compounds of formula I.

The compounds of formula I are useful in the treatment of hyperproliferative skin disease, e.g., psoriasis, in mammals, e.g., humans, which may be demonstrated by their 5-lipoxygenase inhibitory activity as discussed above or by the Arachidonic Acid Mouse Ear Test as described below.

ARACHIDONIC ACID MOUSE EAR TEST, MATERIALS AND METHODS

Charles River, female, CD, (SD) BR mice, 6 weeks old, are caged 8 animals/group and allowed to acclimate 1–3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by applying 10 ml of AA to both surfaces of one ear (4 gm total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp. 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean±standard error and all possible comparisons are made via Duncan's Multiple Range Statistic.

The immunomodulating activity of the compounds of formula IIa may be demonstrated by their inhibition of T cell and B cell proliferation in the following test.

T- AND B-CELL MITOGENIC RESPONSIVENESS

Spleen cells were obtained from six to eight week old C57 B1/6J male mice. One million viable spleen cells were cultured in triplicate in microtest II plates in the presence of 1 μg concanavalin A (Con A) 0.25 μg phytohemagglutinin (PHA) or 1.5 μg lipopolysaccharide (LPS) for 72 hr at 37° C. The total volume was 0.2 ml. One microcurie $^3$H-thymidine (specific activity, 2.0 Ci/mmole) was added for the last 16 hr of incubation. The cells were harvested and processed on a mash II harvester. A stock solution of $1 \times 10^{-2}$ μg. of the drug was prepared in distilled water and then diluted with medium to the appropriate concentration. Drugs were added at the initiation of culture at concentrations of 0.01 to 100 μg. Immunomodulatory activity was determined by measuring percent inhibition of T cell proliferation for Con A and PHA and B cell proliferation. Compounds exhibiting >60% inhibition were determined to have great immunomodulating activity.

GENERAL SYNTHETIC PREPARATIONS

The tetrahydrofuran compounds of the present invention represented by formulas I, II and IIa may be synthesized utilizing the sequence of reactions illustrated in the following Schemes 1 and 2 (Type i), 3 (Type ii) and 4 (Type iii). The oxetane compounds of the present invention (Type iv) represented by formulas I and IIa may be synthesized utilizing the sequence of reactions illustrated in Scheme 5.

Scheme 1 (Type i)

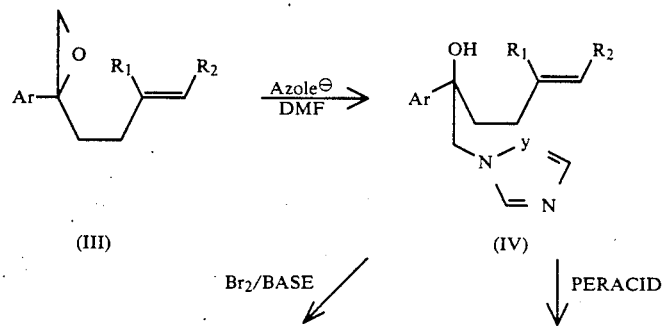

Scheme 1 (Type i)

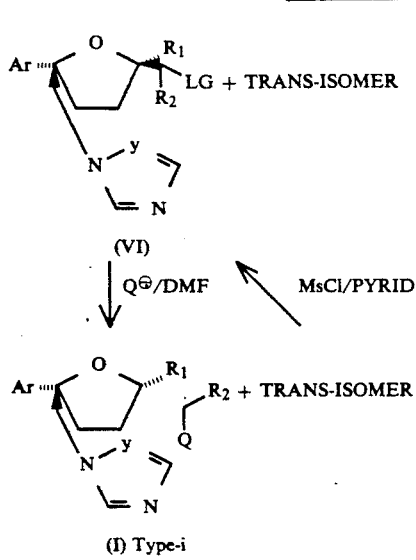

(VI)

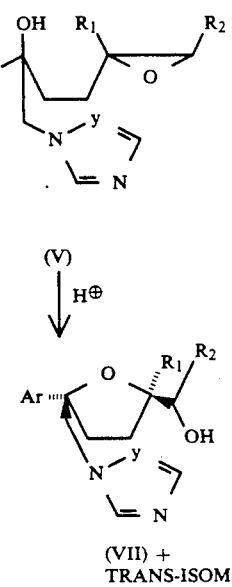

(V)

(I) Type-i (VII) + TRANS-ISOMER

In the formulas listed in the Schemes, Ar, Y, $R_1$, $R_2$ and Q have the same meaning as defined hereinabove.

As used herein, the term "leaving group" (LG) means leaving groups readily removable under conventional conditions well known to those skilled in the organic synthetic arts so as to form the compound represented by formula I. Typical suitable leaving groups include but are not limited to halide especially bromide but also iodide, trifluoromethylsulfonyloxy, and 4-methylphenylsulfonyloxy.

Compound III may be prepared by treating ketones of the formula Ar

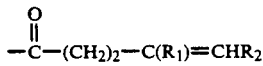

with dimethyloxosulfonium methylide [produced and used as described in European Patent Application 97425 published Jan. 4, 1984] to produce the oxirane of formula III. See for example, Example 1 herein. Compounds of formula III are treated with the appropriate azole anion in aprotic solvents such as dimethylformamide (hereinafter "DMF") to produce the tertiary alcohol of formula IV. The tertiary alcohol of formula IV may be treated with halogen such as bromine and an inert solvent such as methylene chloride and base such as sodium carbonate to produce the tetrahydrofuran of formula VI wherein LG is Br, as well as the corresponding trans-isomer. The tertiary alcohol of formula IV may also be treated with a peracid such as m-chloroperbenzoic acid (MCPBA) in an inert solvent such as methylene chloride or chloroform to produce the oxirane of formula V. The oxirane of formula V may be treated with acid in an inert solvent such as methylene chloride to produce the cis-tetrahydrofuran compound of formula VII plus the corresponding trans-isomer. Typical suitable acids include mineral acids such as HCl, HBr, $H_2SO_4$ and sulfonic acids such as p-toluene sulfonic acid. The mixture of tetrahydrofuran cis-VII and trans-VII may be separated by, for example, conventional chromatographic techniques well known to synthetic organic chemists or may be converted into compounds of formula I (A is O, B and C are each $CH_2$) by converting them to VI (LG = $OSO_2CH_3$) followed by reaction with the anions represented by $Q^-$, anions, such as

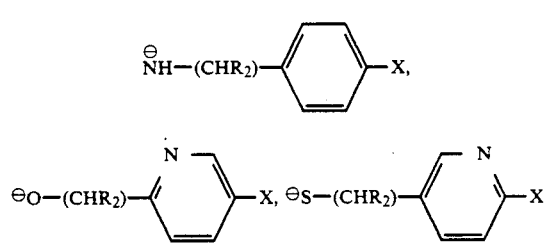

or $—W—CH_2—(C\equiv C)_r—Ar$, $—W—CH_2—(C\equiv C)—C(R_1)_t$, $—W—CH_2—CH=CH—C\equiv(R_1)_t$, $—W—CH_2(C\equiv C)CH_2NR_6R_7$ (wherein W, Ar, P, r, t, $R_1$, $R_6$ and $R_7$ are as defined hereinabove) which may be prepared from the corresponding acids by reaction with bases such as alkali metal hydride, e.g. NaH, or alkaline earth hydride, e.g. $CaH_2$ or alkali metal amides, e.g. $NaNH_2$, in aprotic solvents such as DMF. The reaction of $Q^{31}$ with cis-VI/trans-VI may be carried out in aprotic solvents such as DMF or DMSO at temperatures between 20° C. and 100° C. The mixtures of cis-I and trans-I may be isolated and separated using standard separation techniques such as chromatography.

the Cis- and trans-tetrahydrofuran compounds of formula VII may be treated with methylsulfonyl chloride (MsCl) in the presence of base e.g. pyridine to produce the mesylate of formula VI (X=$OSO_2CH_3$). Compound VI may be treated with $Q^{31}$, as defined hereinabove, in an aprotic solvent to produce the compounds of formula I (A=O, B=C=$CH_2$).

The compounds of formula I have at least two asymmetric carbon atoms in their structures, namely those located at 2- and 5-positions of Type i or the 2- and 4-positions of the five membered ring compounds Type ii and iii, and consequently can exist in different stereochemical isomeric forms. The stereochemical isomeric forms of I and the pharmaceutically acceptable acid addition salts thereof are intended to be within the scope of this invention.

The stereomeric isomers of I, are denoted as cis- and trans- forms respectively, according to the rules described in C.A., 76, Index Guide, Section IV, p. 85 (1972), and may be separated by conventional methods. Appropriate separation methods which may advantageously be employed therefore include, for example, selective crystallization and chromatography separation, e.g. column chromatography.

Since the stereochemical configuration is already fixed in the intermediates (VI and VII) it is also possible to separate cis- and trans- forms at this or even an earlier stage, whereupon the corresponding forms of (I) may be derived therefrom in the previously indicated manner. The separation of cis- and trans-forms of such intermediates may be performed by conventional methods as described hereinabove for the separation of cis- and trans- forms of the compounds of formula I.

It is evident that the cis- and trans- forms of I may be further resolved into their optical isomers, (+)-cis, (−)-cis, (+)-trans, and (−)-trans by the application of methodologies known to those skilled in the art.

Scheme 2 illustrates a stereospecific synthesis of compounds of formula I, Type i (cis-series, A=Oxygen).

Schemes 3 and 4 illustrate sequences of reactions useful for preparation of Types ii and iii of the compounds of formula I

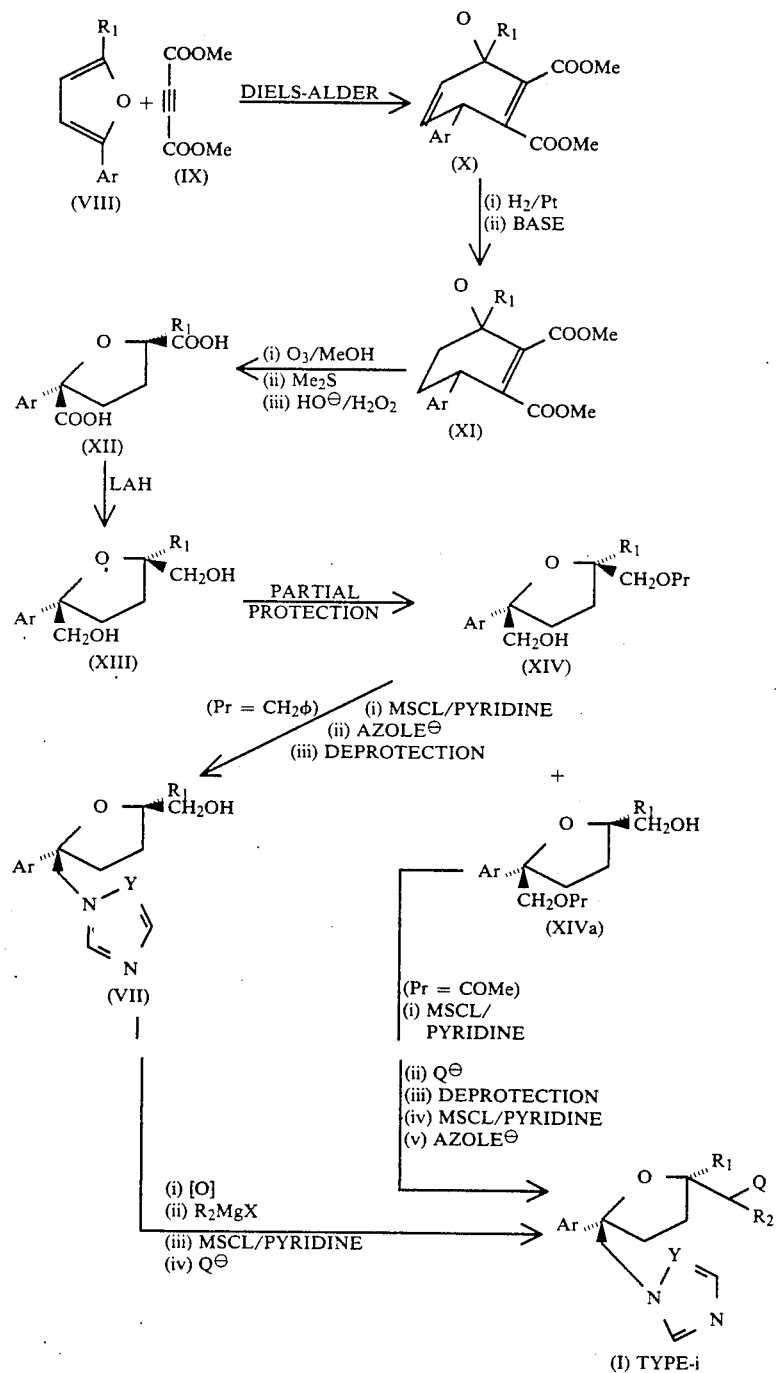

Scheme 2 (Type i)

As depicted in Scheme 2, Diels-Alder reaction between compounds of formula VIII with a dieneophile such as dimethyl acetylenedicarboxylate of formula IX in aqueous medium [according to procedure of Rideout and Breslow, *J.A.C.S.* 102, 7816 (1980)] produces an adduct of formula X. Semi-hydrogenation of X over Adam's platinum catalyst followed by aqueous hydrolysis with an alkali metal hydroxide gives the diacid of formula XI. Ozonolysis of XI in methanol/methylene chloride followed by dimethylsulfide work-up yields a dipyruric acid which is not isolated but is treated directly with hydrogen peroxide under basic conditions to give the tetrahydrofuran diacid of formula XII in the cis-form only. The cis-diacid XII or its corresponding diester can be reduced with a reagent such as lithium aluminium hydride (LAH) to the diol of formula XIII. Treatment of diol XIII with one equivalent of a protecting reagent (Pr) in the presence of base or acetic anhydride such as benzyl bromide in presence of base or acetic anhydride can give XIV and/or XIVa. Both compounds XIV and XIVa are useful key intermediates for preparing compounds of the present invention. For example, the free hydroxy group of XIV is first converted to a leaving group such as $-OSO_2Me$, $-OSO_2CF_3$, I or Br using well known procedures and reagents. Displacement of the leaving group with 1-H-azolyl anion according to procedure of U.S. Pat. No. 4,518,415 followed by debenzylation using standard conditions gives the (+) cis-VII. Introduction of the $R_2$ moiety is accomplished by methodology well known in art as shown in Scheme 2 to provide compounds of Type i in a stereospecific manner. Alternatively, when using XIVa, the group Q is introduced first via mesylation of free hydroxy group followed by nucleophilic displacement of the mesyl group with $Q^-$. The resulting compound is deprotected using standard conditions, mesylated and treated with azolyl anion to provide compounds of Type i in a stereospecific manner. If desired, introduction of $R_2$ can be accomplished by the same sequence of reactions on XIVa as already described for VII.

Compound XII can be converted regio specifically into a lactone [not shown in Scheme 2, but see Example 69(a)+, (b)]. The lactone can be converted in the cis-compound of formula VII by methods well known to those skilled in the art. The cis compound of formula VII is thereafter converted into the cis-compound of formula I (type i) without production of the corresponding trans-isomer.

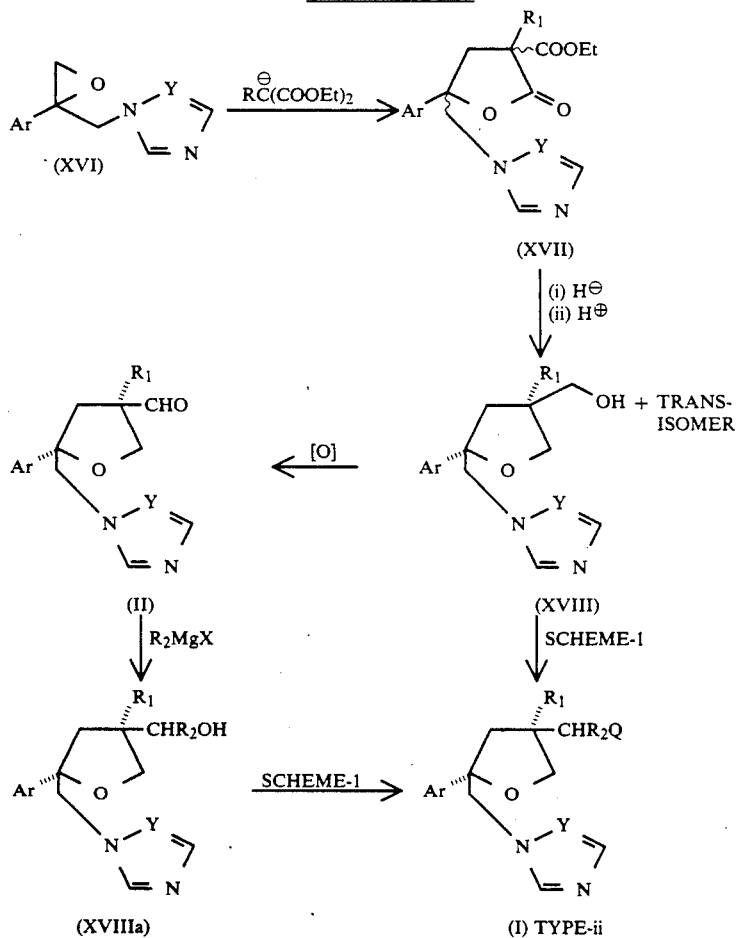

Scheme 3 illustrates the sequence of reactions for preparation of the cis- and trans-forms of Type ii of the compounds of Formula I ($A=C=CH_2$; $B=O$).

The oxirane of formula XVI (prepared according to U.K. Patent G.B. 2099818A) is treated with an $R_1$-substituted dialkyl melonate anion in DMF or DMSO to produce the (±)-cis lactone of formula XVII in admixture with the corresponding trans-isomer. Reduction of XVII with reagents such as lithium aluminium hydride or lithium borohydride gives a triol intermediate which is not isolated but is treated with an acid (e.g. conc. HCl) to provide the (±)-cis-tetrahydrofuran of formula XVIII in admixture with its (±)-trans-isomer. Oxidation of XVIII to the aldehyde of formula II followed by treatment with R₂MgX (a Grignard reagent) provides XVIIIa. Treatment of either XVIII or XVIIIa in a manner analogous to treatment of VII according to Protection of the hydroxy moiety, followed by treatment with Q⁻ and deprotection with acid gives (±)-cis- and (±)-trans- substituted furanmethanol of formula XXVII. Introduction of the azole moiety is accomplished by mesylation of the free hydroxy group in XXVII with an azole anion to give Type iii compounds of formula I

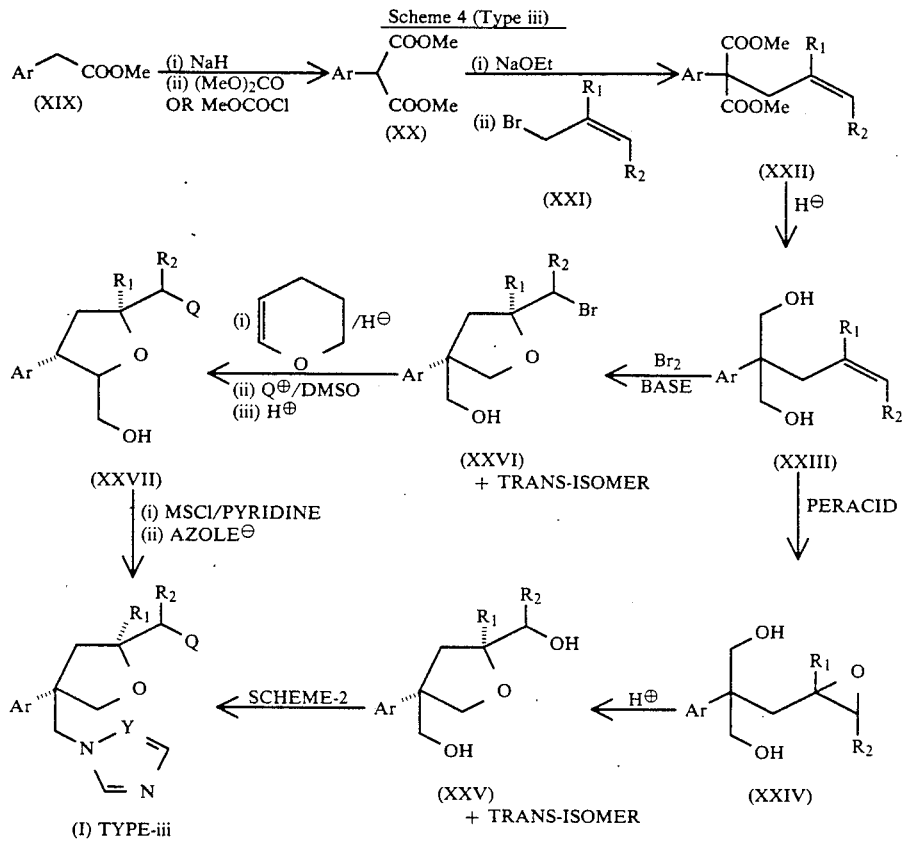

Scheme 1 results in compounds of Type-ii.

Scheme 4 illustrates the sequence of reactions for preparation of the (±)-cis and (±)-trans-isomers of Type iii of the compounds of formula I (A=B=CH₂; C=Oxygen).

The readily available aryl methyl acetates of formula XIX may be treated with dimethyl carbonate or methyl chloroformate in the presence of base (e.g. NaH in DMF) to produce the aryl-substituted malonate of formula XX. Alkylation of XX under standard conditions (e.g. NaOET NaH/DMF) with the R₁,R₂-substituted allyl bromide of the formula XXI (available commercially from e.g. Aldrich) produces the substituted butene of formula XXII. Selective reduction of malonate ester moiety with a metal hydride reducing reagent such as LiBH₄, Ca(BH₄)₂, lithium aluminium hydride or lithium disobutylaluminium hydride provides the 1,3-propanediol of formula XXIII.

Treatment of XXIII with a peracid such as m-chloroperbenzoic acid gives the epoxide of formula XXIV which upon treatment with an acid as in Scheme 1 for conversion of V into VII provides the (±)-cis-diol of formula XXV as well as its (±)-trans-isomer. Treatment of XXV according to Scheme 2 results in compounds of Type iii.

Treatment of XXIII with bromine and base, e.g. pyridine gives the (±)-cis-isomer of the furanemethanol of formula XXVI in admixture with its (±)-trans-isomer.

Scheme 5 illustrates the sequence of reactions for the preparation of the cis- and trans-forms of the oxetane compounds of formula I (type iv) (A=oxygen, B=CH₂ and C= a direct bond) as well tetrahydrofuran compounds of formula I (Type i), A=oxygen, B=C=—CH₂—.

The chloromethyl aryl ketones of formula XXVIII are reacted with the Grignard reagent of R₁,R₂-substituted allyl bromide of formula XXI to produce the substituted pentenol of formula XXIX (S=1). Reaction of XXIX and XXIXa with an azole anion followed by treatment of the so-formed product with peracid gives the 1,2-oxo-4-aryl-5-azol-1-yl-4-pentenol of formula XXX. Treatment of XXX with Q⁻ with DMSO produces isomeric 2,4-pentanediol compounds of formulas XXXI (isomer-1) and XXXII (isomer-2). Compounds of formula XXXI and XXXII exhibit broad spectrum antifungal activity, in conventional antifungal screening tests, against human and animal pathogens, such as the following: *Aspergillus, Candida, Epidemophyton, Geotrichum, Monosporium, Rhodotorula, Saccharomyces, Torulopsis* and *Trichophyton*.

The compounds of formulas XXXI and XXXII exhibit topical and oral antifungal activity in in vivo tests in animals that is at least comparable to or better than that for ketoconazole, a commercial product.

Treatment of XXXI or XXXII with tosyl chloride and base converts the 2-hydroxyl group into a tosylate which upon treatment with an alkyl lithium reagent e.g. n-butyl lithium produces (±)-cis-and (±)-trans-oxetanes of formula I Type iv by intramolecular nucleophilic displacement of the tosyl group by the hydroxy anion at C-4.

Tetrahydrofurans of formula I (type i) may be made using Scheme 5 by substitution in the first reaction of a $R_1,R_2$-substituted butenyl bromide (S=2) for the allyl bromide of XXI (S=1).

methylene chloride (1L), m-chloroperbenzoic acid (24.2 g) was added with cooling (bath temp. ~0° C.) in small portions over a period of 20 minutes. The reaction mixture was allowed to warm up to room temperature and stirred overnight. After a total of 24 hours of stirring, thin layer chromatographic analysis (TLC) of the reaction mixture showed the presence of starting material. Additional m-chloroperbenzoic acid (7 g) was added and stirring was continued for an additional 12 hours; no starting material was detected by TLC. The homogeneous reaction mixture was washed with 500

SCHEME 5

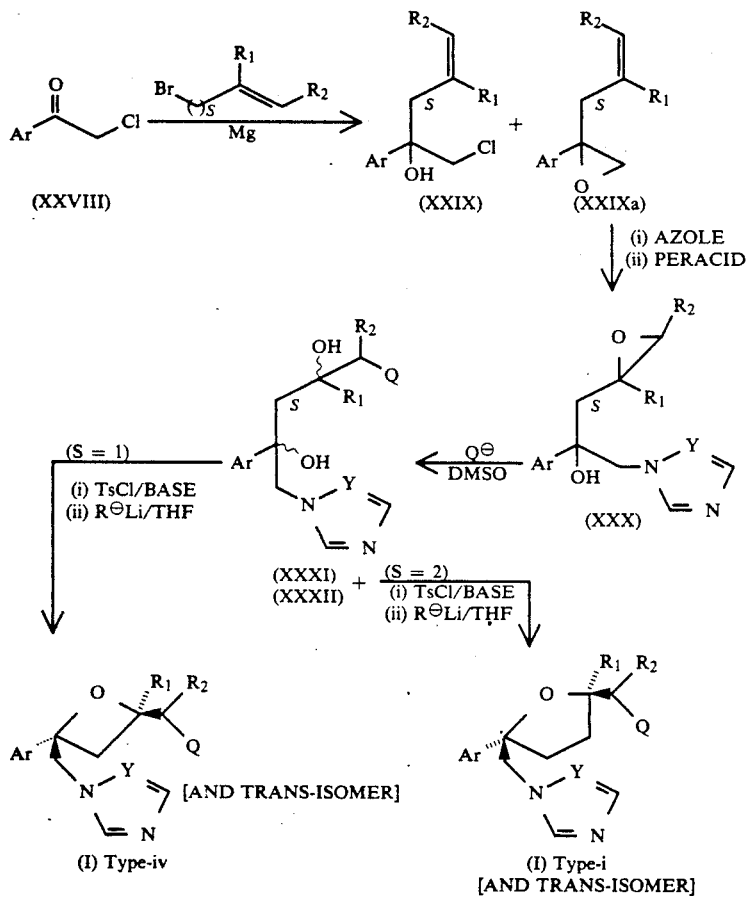

GENERAL EXPERIMENTAL

In the following Examples, compounds having Ar equal to 2,4-difluorophenyl may be prepared by substituting an equivalent amount of the 2,4-difluorophenyl substituted starting material corresponding to the 2,4-dichlorophenyl substituted starting material employed in such Examples and thereafter using analogous procedures well known to those skilled in the art. In a similar fashion, compounds having Ar equal to 2,4-dichlorophenyl may be prepared by substituting an equivalent amount of the 2,4-dichlorophenyl substituted starting material for the corresponding 2,4-difluorophenyl starting material used.

EXAMPLE 1

α-(2,4-Dichlorophenyl)-α-(2-oxiranylethyl)-β-(1H-1,2,4-triazol-1-yl)-ethanol

To a stirred solution of α-(2,4-dichlorophenyl)-α-(3propen-1-yl)-β-[1H-1,2,4-triazol-1-yl]ethanol (40 g) in mL portions of saturated NaHSO$_3$, saturated Na$_2$CO$_3$, brine and dried over Na$_2$SO$_4$. The solution was filtered free of Na$_2$SO$_4$ and evaporated in vacuo at 35°–40° C. to provide the title compound as a yellow tarry solid (47 g) which was used as such in Example 2.

EXAMPLE 2

(±)-cis and trans-(±)-5-(2,4-Dichlorophenyl)-tetrahydro-5-[(1H-1,2,4-triazol-1-yl)methyl]-2-furanmethanol A solution of the title compound of Example 1 (10.49 g) in methylene chloride (400 ml) was treated with p-toluenesulfonic acid (6.1 g) and the so-formed mixture was stirred for 15 hours. The solution was washed with saturated NaHCO$_3$ (200 ml), water (100 ml) and then dried (MgSO$_4$). After removal of MgSO$_4$ by filtration, the filtrate was evaporated in vacuo to dryness. The resulting oil was chromatographed over silica gel (350 g) using 2% methanol in methylene chloride as eluent. Fractions containing the (±)-cis- and (±)-trans- isomers of the title compound were combined in two flasks to give 2.5 g of the less polar cis-isomer, m.p. 130°-131° C., and 2.3 g of the more polar trans-isomer, m.p. 104°-106° C.

EXAMPLE 3

(±)-cis-5-(2,4-Dichlorophenyl)tetrahydro-5-[(1H-1,2,4-triazol-1-yl)methyl]-2-furanmethanol, methanesulfonate 5.0 g (15.2 mmole) of the title compound of Example 2 was dissolved in 50 ml of pyridine. The pyridine mixture was cooled to 0°-5° C. and 1.47 mL (19.0 mmole) of methanesulfonyl chloride was added and the so-formed reaction mixture was stirred 3 hours at 0°-5° C. The pyridine was evaporated under high vacuum. The residue was dissolved in 500 mL of methylene chloride and extracted with 250 mL of 5% NaHCO$_3$ followed by 250 ml of H$_2$O. The methylene chloride solution was dried over anhydrous MgSO$_4$ and concentrated to give 6.25 g of the title compound, M/e, M+ 407.

EXAMPLE 4

(±)-cis- and (±)-trans-1-[[2-(2,4-Dichlorophenyl)-tetrahydro-5-(iodomethyl)-2-furanyl]methyl]-(1H-1,2,4-triazole To a two-phase system containing α-(2,4-dichlorophenyl)-α-(3-propen-1-yl)-β-[1H-1,2,4-triazol-1-yl]ethanol (500 mg) in methylene chloride (16 mL) and NaHCO$_3$ (1.5 g) in water (29 mL) was added over 2 hours (with stirring) a solution of iodine (447 g) in methylene chloride (18 mL). The reaction mixture was stirred overnight at room temperature. The organic phase was separated, washed with 5% sodium thiosulfate and dried over MgSO$_4$. Evaporation in vacuo provided an oil containing unchanged starting material and the two isomers of the title compound. Preparative TLC using 2% methanol in methylene chloride provided 76 mg of the less polar cis-isomer as a thick oil, and 238 mg of the more polar 238 mg trans-isomer as a thick oil.

EXAMPLE 5

(±)-cis- and (±)-trans-1-[[5-Bromomethyl)-2-(2,4-dichlorophenyl)-tetrahydro-2-furanyl]methyl]-1H-1,2,4-triazole Bromine (276 mg) in methylene chloride (5 mL) was added dropwise to a stirred solution of α-(2,4-dichlorophenyl)-α-(3-propen-1-yl)-β[1H-1,2,4-triazol-1-yl]ethanol (474 mg) in methylene chloride (5 mL) at 0° C. The reaction mixture was stirred for 1 hour, diluted with methylene chloride (70 mL), washed with water (30 mL) and thereafter saturated NaHCO$_3$. The organic phase was dried (MgSO$_4$) and evaporated in vacuo to provide a thick oil which was a mixture of unchanged starting material and the cis- and trans-isomers of the compound. Chromatography on preparative silica gel thin layer plates using ethyl acetate:n-hexanes provided the pure isomers 29 mg of the less polar cis-isomer as a thick oil, and 62 mg of the more polar trans-isomer as a thick oil.

EXAMPLE 6

(±)-cis-1-[4-[[2-(2,4-Dichlorophenyl)tetrahydro-2-[(1H-1,2,4-triazol-1-yl)methyl]-5-furanyl]methoxy]-phenyl]-4-yl-1-methylethyl)piperazine)

Method A 3.29 g (14.9 mmole) of 1-(4-hydroxyphenyl)-4-(1-methylethyl)piperazine was suspended in 100 mL of DMSO. 0.66 g (16.4 mmole) of NaH (60% oil dispersion) was added and the suspension so formed stirred for 30 min. at room temperature. 3.29 g (14.9 mmole) of the title compound of Example 3 was added and the so formed mixture stirred at 75° for 1 hr. The mixture was poured into 1-liter of methylene chloride and the methylene chloride layer extracted with 3-1 liter portions of H$_2$O. The methylene chloride layer was dried over anhydrous MgSO$_4$ and concentrated to a gum. The gum was chromatographed on silica gel, eluting with a 2% MeOH/H$_2$CCl$_2$ containing 2 ml of conc. NH$_4$OH per liter of solution. There was obtained 5.02 g of material which was treated with charcoal and recrystallized from hexane/methylene chloride to give the title compound as a solid, m.p. 107°-109° C., M/e, M+ 531.

Method B

A solution of (±)-cis-1-[4-[[2-(2,4-dichlorophenyl)-tetrahydro-2-[(1H-1,2,4-triazol-1-yl)methyl]-5-furanyl]methoxy]phenyl]piperazine, (810 mg) in methanol (8 mL) was adjusted to pH 6.7 with a HCl/isopropanol solution. Acetone (0.20 mL) and sodium cyanoborohydride (100 mg) were added and the reaction mixture was stirred at room temperature for 72 hours. Methanol was removed on a rotary evaporator at reduced pressure and water (50 mL) was added. The pH of the aqueous phase was adjusted to 9 with 5% aqueous potassium carbonate and extracted with methylene chloride (75 ml×2). The methylene chloride extract was dried (MgSO$_4$) and evaporated in vacuo to provide the crude product (820 mg) which was chromatographed on silica gel (60 g). Elution with 2-4% methanol in methylene chloride provided in some fractions the desired title compound (225 mg) which was treated with etheral HCL to give the trihydrochloride salt of the title compound as a white solid, m.p. 170°-175° C.

Elemental analysis: C,50.90; H,5.83; N,10.9; C$_{27}$H$_{33}$N$_5$O$_2$.3HCl requires: C,50.68; H,5,68; N,10.94

EXAMPLE 7

(±)-cis-1H-1,2,4-Triazole-[[2-(2,4-dichlorophenyl)tetrahydro-5-[[4-(1H-imidazol-1-yl)phenoxy]methyl]-2-furanyl]methyl]-

To a solution of 236 mg (1.47 mmole) of 4-(imidazol-1-yl)phenol dissolved in 10 ml of DMSO, 78 mg (1.61 mmole) of NaH (50% oil dispersion) was added and the reaction mixture so formed was stirred for 30 min. at room temperature. 500 mg (1.23 mmole) of the title compound of Example 3 was added and the reaction mixture was stirred at 75° C. for 10 hours. The reaction mixture was poured into 250 ml of methylene chloride which was extracted with three 250 ml portions of H$_2$O. The methylene chloride was dried over anhydrous MgSO$_4$ and concentrated to a gum. The gum was chromatographed on silica gel, eluting with 1% MeOH/H$_2$CCl$_2$ containing 1 ml of con. NH$_4$OH per liter of solution to give 379 mg of the title compound, M/e, M+ 471.

EXAMPLE 8

(±)-cis-1H-1,2,4-Triazole, 1-[4-[[2-(2,4 dichlorophenyl)tetrahydro-2-[(1H-1,2,4-triazol-1-yl)methyl]-5-furanyl]methoxy]phenyl]

286 mg (1.78 mmole) of 4-(1H-1,2,4-triazol-1-yl)phenyl was dissolved in 10 mL of DMSO. 103 mg (2.14 mmole) of NaH (50% oil dispersion) was added and the so formed reaction mixture stirred 30 min. at room temperature. 600 mg (1.48 mmole) of the title compound of Example 3 was added and the so formed reaction mixture stirred the reaction mixture at 75° for 3 hours. The reaction mixture was poured into 250 ml of methylene chloride which was extracted with three 250 ml portions of $H_2O$. The methylene chloride was dried over anhydrous $MgSO_4$ and concentrated to a gum. The gum was chromatographed on silica gel, eluting with 1% $MeOH/H_2CCl_2$ containing 1 mL of con. $NH_4OH$ per liter of solution to give 434 mg of the title compound, M/e, $M^{30}$ 472.

EXAMPLE 9

(±)-cis-4-[[2-(2,4Dichlorophenyl)tetrahydro-2-[(1H-1,2,4-triazol-1-yl)methyl]-5-furanyl]-methoxy]benzamide 260 mg (190 mmole) of 4-hydroxybenzamide was dissolved in 10 mL of DMSO. 76 mg (1.90 mmole) of NaH (60% oil dispersion) was added and the reaction mixture so formed stirred 30 min. at room temperature. 813 mg (2.0 mmole) of the title compound of Example 3 was added and the reaction mixture stirred at 75° C. for 3 hours. The reaction mixture was poured into 250 mL of methylene chloride and 250 ml of $H_2O$. 5 ml of 50% NaOH were added and the so formed mixture was stirred 5 min. The methylene chloride layer was separated and washed with another 250 ml of $H_2O$. The methylene chloride was dried over anhydrous $MgSO_4$ and concentrated to a gum. The gum was chromatographed on silica gel, eluting with 1% $MeOH/H_2CCl_2$ containing 1 mL con. $NH_4OH$ per liter of solution to give 270 mg of the title compound, M/e, $M^+$ 448.

EXAMPLE 10

(±)-cis-4-[4-[4-[2-(2,4-Dichlorophenyl)tetrahydro-2-[(1H 1,2,4-triazol-1-yl)methyl]-5-furanyl]methoxy]-phenyl]-1-piperazinyl]phenyl]-2,4-dihydro-2-(1-methylpropyl)-3H-1,2,4-triazol-3-one To a solution of 2,4dihydro-4[4-[4-(4-hydroxyphenyl)-1-piperazinyl]-phenyl]-2-(1-methylpropyl)-3H-1,2,4-triazol-3-one (prepared as described in J. Herrres et al., *J. Med. Chem.*, 1984, Vol. 27, P 894–900) (1.299 g, 3.3 mmole) in 50 ml of dry dimethyl sulfoxide (DMSO), NaH (0.087 g, 3.6 mmole) was added and reaction mixture so formed was stirred at room temperature for 1 hour. A solution of (±)-cis-2-furanmethanol, 5-(2,4-dichlorophenyl)-tetrahydro-5-[(1H-1,2,4-triazol-1-yl], methyl]methane sulfonate (1.218 g, 3 mmole) in 25 mL dry DMSO was added dropwise at room temperature. The reaction mixture was stirred at 80° C. for 5 hours. The mixture was then cooled to room temperature, diluted with 500 ml EtOAc and washed with $H_2O$ several times. The organic phase was dried over $MgSO_4$. Evaporation of solvent gave gum. The gum was stirred with ether to give 0.700 g of the title compound as a solid, M/e, $M^+$ 704.

EXAMPLE 11

(±)-cis-1-Acetyl-4-[4-[[2-(2,4-dichlorophenyl)tetrahydro2-[(1H-1,2,4-triazol-1-yl)methyl]-5-furanyl]methoxy]phenyl]piperazine

Method A

To a solution of 1-acetyl-4-(4-hydroxyphenyl)-piperazine (1.145 g, 5.2 mmole) in 15 mL of dry DMSO, NaH (0.137 g, 5.7 mole) was added. The mixture so formed was stirred at room temperature for 1 hour. A solution of the title compound of Example 3 (1.909 g, 4.7 mmole) in 25 ml dry DMSO was added dropwise at 10° to 15° C. The so formed mixture was allowed to warm up to room temperature and then stirred at room temperature for 15 minutes. The mixture was then stirred at 80° C. for 5 hours. The mixture was cooled to room temperature, diluted with 500 ml ethyl acetate (EtOAc) and washed with saturated NaCl solution several times. The organic phase was dried over $MgSO_4$. Evaporation of solvent gave gum which upon silica gel chromatography, eluting with methylene chloride/methanol 1%/0.1 ml $NH_4OH$ have gum. The gum was then stirred with 100 ml diethyl ether/methanol 5% to give 1.0 g of the title compound as solid, M/e, $M^+$ 531.

Method B

A solution of 656 mg of 5-(2,4-dichlorophenyl)tetrahydro-5-[(1H-1,2,4-triazol-1-yl)methyl]-2furanmethanol, 524 mg of triphenylphosphine, 441 mg of 1-acetyl-4-(4-hydroxyphenyl)-piperazine and 0.4 ml diisopropylazodicarboxylate in 35 ml tetrahydrofuran [redistilled over lithium aluminum hydride ($LiAlH_4$) ] was stirred overnight at room temperature. Tetrahydrofuran was evaporated in vacuo (temp. 70°–75° C.) and the residue was chromatographed over silica gel (120 mL, column width 3 cm). Elution with 2–3% methanol in methylene chloride gave a partially purified product. Rechromatography on preparative thin layer silica gel plates provided the title compound as solid (60 mg). The molecular formula was determined by mass spectrum to be $C_{26}H_{29}O_3H_5Cl_2$.

Method C

Sodium hydride (20 mg; 60% oil dispersion) was added to a solution of 1-acetyl-4-(4-hydroxyphenyl)-piperazine (113 mg) in dimethylformamide (2 ml). The mixture was heated at 50° C. for 1 hour, allowed to cool to room temperature and then treated with 1-[[2-(2,4-dichlorophenyl)tetrahydro-5-(iodomethyl)-2-furanyl]-methyl]1H-1,2,4-triazole, (150 mg) and 18-crown-6 ether (90 mg). The reaction was heated at 80°60 C. for 72 hours. Dimethylformamide (DMF) was evaporated in vacuo and the residue was treated with water (30 mL). The aqueous phase was extracted with ethyl acetate (50 ml×2). The organic extract was dried ($Na_2SO_4$) and evaporated to dryness in vacuo to provide the crude product. Chromatography on silica gel (15 mL) using methylene chloride:methanol (5:1) as eluent provided in one of the fractions pure title compound (20 mg) identical to the product obtained by methods A and B of Example 11.

EXAMPLE 12

(±)-cis-2-[[[2-(2,4-Dichlorophenyl)tetrahydro-2-[(1H-1,2,4-triazol-1-yl)methyl]-5-furanyl]-methyl]thio]pyridine To a solution of 2-mercaptopyridine (0.333 g) 3 mmole) in 5 mL dry DMSO under argon (Ar) was added NaH (0.079 g, 3.3 mmole) at 0° to 5° C. The reaction mixture so formed was stirred at 0° to 5° C. for 30 minutes. A solution of the title compound of Example 3 (0.609 g, 1.5 mmole) in 10 mL of dry DMSO was added dropwise at 5° to 10° C. under Ar. The mixture was heated at 60° C. for 4 hours. The mixture so formed was allowed to cool to room temperature, diluted with 250 mL of $CH_2Cl_2$ and washed with $H_2O$ several times. The organic phase was dried over $MgSO_4$. Evaporation of solvent gave gum which upon silica gel chromatography, eluting with methylene chloride/methanol 1%/0.1 ml $NH_4OH$ gave 0.218 g of the title compound as gum, M/e, $M^+$ 422.

EXAMPLE 13

(±)-cis-1-[4-[4-[[2-(2,4-Dichlorophenyl)tetrahydro-2-[(1H)-1,2,4-triazol-1-yl)methyl]-5-furanyl]methyl]-1-piperazinyl]phenyl]ethanone A mixture of the title compound of Example 3 (1 g, 2.46 mmole, 4-piperazinoacetophenone (1 g, 4.89 mmole) and triethylamine (0.5 g, 4.9 mmole) in toluene (20 mL) was heated under reflux for seven days. The reaction mixture was evaporated to dryness in vacuo. The oily residue was extracted with methylene chloride and the organic layer was washed with water, dried ($MgSO_4$), and concentrated in vacuo to give an oil. The oil was subjected to silica gel chromatography, eluting with methylene chloride/methanol 1% to give the title compound as an oil (0.42 g). M/e, $M^{30}$ 514.

EXAMPLE 14

(±)-cis-1-[[5-(Azidomethyl)-2-(2,4-Dichlorophenyl)-tetrahydro-5-2-furanyl]methyl]-1H-1,2,4-triazole 2.03 g (5.0 mmole) of the title compound of Example 3 was dissolved in 25 mL of DMF. Sodium azide (0.65 g, 10.0 mmole) was added and the so formed mixture stirred at 100° C., under Ar, for 10 hours. The reaction mixture was poured into 300 ml of ethyl acetate (EtOAc) and 200 ml of $H_2O$, the so formed mixture was stirred 5 min. The EtOAc layer was separated and washed with another 200 ml of $H_2O$. The EtOAc layer was dried over anhydrous $MgSO_4$ and concentrated to give 1.67 g of the title compound, M/e $M^+$ 354.

EXAMPLE 15

(±)-cis-5-(2,4-Dichlorophenyl)tetrahydro-5-[1H-1,2,4-triazol-1-yl]methyl]-2-furanmethanamine 1.67 g (4.73 mmole) of the title compound of Example 13 dissolved in 50 mL of absolute ethanol was hydrogenated for 3 hours at 26° C. over 200 mg of 5% Pd/C catalyst. The solution was filtered to remove the catalyst and the solution concentrated to give 160 g of the title compound, M/e, $M^+$ 328.

EXAMPLE 16

(±)-cis-N-[[2-(2,4-Dichlorophenyl)tetrahydro-2-[(1H-1,2,4-triazol-1-yl)methyl]-5-furanyl]methyl]trifluoroacetamide A solution of 6.28 g (18.9 mmole) of cis 2-furanmethanamine, 5-(2,4-dichlorophenyl)tetrahydro-5-[1H-1,2,4-triazol-1-yl]methyl] in 250 mL of $H_2CCl_2$ was cooled to 0°–5° C. and 3.19 ml (22.9 mmole) of triethylamine and 2.94 ml (20.8 mmole) of trifluoroacetic anhydride was added thereto. The so formed mixture was stirred at 0°–5° C. for 3 hours. The reaction mixture was poured into 250 mL of methylene chloride and extracted with two 250 mL portion of $H_2O$. The organic layer was dried over anhydrous $MgSO_4$ and concentrated to give 7.57 g of the title compound, M/e, $M^+$ 424.

EXAMPLE 17

1-Bromo-6,6-dimethyl-2,4-heptadiyne

A solution of 5.0 g (37.3 mmole) of 1-hydroxy-6,6-dimethyl-2,4-heptadiyne and 14.8 g (44.7 mmole) of carbon tetrabromide in 250 mL of $H_2CCl_2$ was cooled to 0°–5° C. and 12.7 g (48.4 mmole) of triphenylphosphine was added thereto. The so formed mixture was stirred for 2 hours at 0°–5° C. The reaction mixture was concentrated to about 50 ml and poured into 1 liter of petroleum ether. The mixture was stirred 15 min. and the petroleum ether was removed by decantation. The oily residue was stirred for 15 min. with another 1 liter of petroleum ether which was decanted off. The combined petroleum ether extracts were concentrated to an oil which was chromatographed on silica gel, eluting with petroleum ether to give 6.87 g of the title compound, M/e, $M^+$ 200.

EXAMPLE 18

(±)-cis-N-[[2-(2,4-Dichlorophenyl)tetrahydro-2-[(1H-1,2,4-triazol-1-yl)methyl]-5-furanyl]methyl]-N-(6,6-dimethyl-2,4-heptadiyn-1-yl)trifluoroacetamide A solution of 7.07 g (16.7) mmole of N-[[2-(2,4-dichlorophenyl)tetrahydro-2-[(1H-1,2,4-triazol-1-yl)methyl]-5-furanyl]methyl]trifluoroacetamide, under Ar, in 50 ml of DMF was cooled to 0°–5° C., 1.0 g (20.9 mmole) of NaH (50% dispersion) was added and the so formed mixture stirred for 30 minutes at room temperature. The reaction mixture was cooled to 0°–5° C. and 5.87 g (34.5 mmole) of 1-bromo-6,6-dimethyl-2,4-heptadiyne in 20 ml of DMF was added thereto dropwise over 30 minutes. The reaction mixture was stirred another 1 hour at 0°–5° C. The DMF was removed under high vacuum. The oily residue was dissolved in 1 liter of methylene chloride and 1 liter of $H_2O$, the so formed mixture stirred for 5 min. The organic phase was separated, dried over anhydrous $MgSO_4$ and concentrated to a gum. The gum was chromatographed on silica gel, eluting with 0.5% $MeOH/H_2CCl_2$ containing 0.5 ml con. $NH_4OH$ per liter of solution to give 3.49 g of the title compound, M/e, $M^+$ 542.

EXAMPLE 19

(±)-cis-5-(2,4-Dichlorophenyl)-N-(6,6-dimethyl-2,4-heptadiyn-1-yl)tetrahydro-5-[(1H-1,2,4-triazol-1-yl)methyl]-2-furanmethanamine To a solution of 3.94 g (7.28 mmole) of the title compound of Example 18 in 450 ml of methanol (MeOH)

was added 50 mL of H₂O and 4.28 g (31.0 mmole) of potassium carbonate. The so formed mixture was stirred, under argon, overnight at room temperature. The MeOH was removed under reduced pressure. The so formed residue was dissolved in 1 liter of H₂CCl₂ and 500 mL of H₂O was added thereto. The so formed mixture was stirred for 5 min. The organic phase was separated, dried over anhydrous MgSO₄ and concentrated to give 3.14 g of the title compound, M/e, M+ 446.

EXAMPLE 20

(±)-cis-5-(2,4-Dichlorophenyl)-N-(6,6-dimethyl-2,4-heptadiyn-1-yl)tetrahydro-N-methyl-5-[(1H-1,2,4-triazol-1-yl)methyl]-2-furanmethanamine To a solution of 3.24 g (7.27 mmole) of cis 2-furanmethanamine, 5-(2,4-dichlorophenyl)-N-(6,6-dimethyl-2,4-heptadiyn-1-yl)tetrahydro-5-[(1H-1,2,4-triazol-1-yl)methyl] in 100 mL of MeOH was added 8.84 mL (109 mmole) of 37% aqueous formaldehyde and the so formed mixture was refluxed for 2 hours. The mixture was cooled to 0°–5° C. and 4.12 g (109 mmole) of sodium borohydride, in 3 portions was added. The reaction mixture was stirred for 1 hour at 0°–5° C. and then 18 hours at room temperature. The MeOH was removed under reduced pressure. The residue was dissolved in 500 ml of H₂CCl₂ and 500 ml of H₂O, the so formed mixture stirred for 5 min. The organic phase was separated, dried over anhydrous MgSO₄ and concentrated to a gum. The gum was chromatographed on silica gel, eluting with 1% MeOH/H₂CCl₂ containing 1 ml of con. NH₄OH per liter of solution to give 1.06 g of the title compound, M/e, M+ 460.

EXAMPLE 21

(±)-cis-5-(2,4-Dichlorophenyl)-N-(6,6-dimethyl-2-hepten-4-yn-1-yl)tetrahydro-N-methyl-5-[(1H-1,2,4-triazol-1-yl)methyl]-2-furanmethanamine To a solution of 100 mg (0.22 mmole) of the title compound of Example 20 in 2 ml of toluene was added 1.1 mL (1.1 mole) of diisobutylaluminum hydride (DIB-AL-H, 1.0M in hexane). The so formed mixture was stirred for 30 min. at room temperature and then overnight at 35°–40° C. The so formed mixture was cooled to room temperature, and 50 mL of H₂CCl₂ and 10 mL of 2% NaOH and 25 mL of H₂O were added thereto and the mixture was stirred for 10 min. The organic phase was separated, washed with 50 mL of H₂O, dried over anhydrous MgSO₄ and concentrated to a gum. The gum was chromatographed on silica gel, eluting with 1% MeOH/H₂CCl₂ containing 1 mL of con. NH₄OH per liter of solution to give 20 mg of the title compound, M/e, M+ 462.

EXAMPLE 22

O-[4'(1H-1,2,4-Triazol-1-yl)phenyl]dimethylthiocarbamate

To a solution of 5.0 g (31.0 mmole) of 4'-(1H-1,2,4-triazol-1-yl)phenol in 100 mL of DMF was added 1.36 g (34.0 mmole) of NaH (60% oil dispersion) and the so formed mixture was stirred 30 min. at room temperature. 5.75 g (46.5 mmole) of dimethylthiocarbamyl chloride was added and the so formed reaction mixture was stirred at 80° C. for 4 hours. The DMF was removed under high vacuum. The residue was dissolved in 500 mL of H₂CCl₂ and 500 mL of H₂O and the so formed mixture was stirred for 5 min. The organic phase was separated and washed with another 500 mL of H₂O and dried over anhydrous MgSO₄ and concentrated to a gum. Trituration of the gum with anhydrous Et₂O gave 5.0 g of the title compound, M/e, M+ 249.

EXAMPLE 23

S-[4'-(1H-1,2,4-Triazol-1-yl)phenyl]dimethylcarbamate 6.1 g (24.6 mmole) of the title compound of Example 22 was stirred at 250°–260° C., under argon, for 1 hour. The reaction mixture was chromatographed on silica gel, eluting with 0.5% MeOH/H₂CCl₂ containing 0.5 mL of con. NH₄OH per liter of solution to give 3.20 g of the title compound, M/e, M+ 249.

EXAMPLE 24

4'-(1H-1,2,4-Triazol-1-yl)benzenethiol

To a solution of 320 g (12.9 mmole) of the title compound of Example 23 in 100 ml of MeOH was added 50 mL of 10% NaOH and the so formed mixture was refluxed for 1 hour. The MeOH was removed under vacuum. Neutralized the pH of the aqueous mixture was adjusted to 7 with 6 N HCl and extracted with 100 mL of methylene chloride. The methylene chloride was washed with 100 mL of H₂O and dried over anhydrous MgSO₄ and solvent removed to give 1.90 g of the title compound, M/e, M+ 178.

EXAMPLE 25

(±)-cis-1-[4-[[[[2-(2,4-Dichlorophenyl)tetrahydro-2-[(1H-1,2,4-triazol-1-yl)methyl]-5-furanyl]methyl]thio]methyl]phenyl]-1H-1,2,4-triazole To a solution of 0.916 g (5.17 mmole) of the title compound of Example 24 in 15 mL of DMSO was added 0.235 g of NaH (60% oil dispersion) and the so formed reaction mixture was stirred for 30 min. at room temperature. 1.91 g (4.70 mmole) of cis-5-(2,4-dichlorophenyl)-5-[(1H-1,2,4-triazol-1-yl)methyl] 2-tetrahydrofuranmethanol, methanesulfonate was added thereto and the so formed reaction mixture stirred at 75° C. for 5 hours. The reaction mixture was poured into 500 mL of methylene chloride and extracted with two 500 mL portions of H₂O. The organic phase was dried over anhydrous MgSO₄ and concentrated to a gum. The gum was chromatographed on silica gel, eluting with 1% MeOH/H₂CCl₂ containing 1 mL con. NH₄OH per liter of solution to give the title compound, M/e, M+ 490.

EXAMPLE 26

(±)-cis-1-[4-[[[[2-(2,4-Dichlorophenyl)tetrahydro-2-[(1H-1,2,4-triazol-1-yl)methyl]-5-furanyl]methyl]-sulfonyl]methyl]phenyl]-1H-1,2,4-triazole To a solution of 450 mg (0.919 mmole) of the title compound of Example 25 in 100 ml of H₂CCl₂ was cooled to 0°–5° C. and 590 mg of m-chloroperoxybenzoic acid (80–85%) was added thereto. The mixture was stirred at 0°–5° C. for 3 hours and then overnight at room temperature. To the reaction mixture there was added 100 mL of H₂CCl₂ and 50 mL of 10% Na₂CO₃. The so formed mixture was stirred for 15 min. The organic phase was separated and washed with 50 mL of H₂O. The organic phase was dried over anhydrous MgSO₄ and concentrated to a gum. Trituration of the gum with anhydrous diethyl ether gave 404 mg of the title compound, M/e, M+ 520.

EXAMPLE 27

(±)-trans-5-(2,4-Dichlorophenyl)tetrahydro-5-[(1H-1,2,4-triazol-1-yl)methyl]-2-furanmethanol, methanesulfonate A solution of 744 mg (2.27 mmole) of trans-2-furanmethanol, 5-(2,4-dichlorophenyl)tetrahydro-5-[(1H-1,2,4-triazol-1-yl)methyl] from Example 2 in 10 mL of dry pyridine was cooled to 0°–5° C. and 0.22 mL (2.84 mmole) of methanesulfonyl chloride was added. The reaction mixture was stirred for 2 hours at 0°–5° C. The pyridine was removed under high vacuum. The residue was dissolved in 100 mL of $H_2CCl_2$ and 50 mL of 5% $NaHCO_3$. The so-formed mixture was stirred for 5 min. The organic phase was separated and washed with 50 ml of $H_2O$, dried over anhydrous $MgSO_4$ and concentrated to give 970 mg of the title compound.

EXAMPLE 28

(±)-trans-1-[4-[[2-(2,4-Dichlorophenyl)tetrahydro-2[(1H-1,2,4-triazol-1-yl)methyl-5-furanyl]methoxy]phenyl]-4-(1-methylethyl)-piperazine A solution of 500 mg (2.27 mmole) of 1-methylethyl-4-(4'-hydroxyphenyl)piperazine and 111 mg (2.83 mmole) of NaH (60% oil dispersion) in 10 mL of DMSO was stirred at room temperature for 1 hour. 970 mg of the title compound of Example 27 dissolved in 10 mL of DMSO was added and the so formed mixture stirred at 75° C. for 3 hours. The reaction mixture was poured into 250 mL of methylene chloride. The organic phase was separated and washed with three 250 ml portions of $H_2O$ and dried over anhydrous $MgSO_4$ and conc. to a gum. The gum was chromatographed on silica gel, eluting with 2% $MeOH/H_2CCl_2$ containing 2 mL conc. $NH_4OH$ per liter of solution to give 487 mg of the title compound, M/e, M+531.

EXAMPLE 29

(±)-cis- and (±)-trans-5-(2,4-Difluorophenyl)-tetrahydro-5-[(1H-1,2,4-triazol-1-yl)methyl]-2-furanmethanol a. 5-Hydroxy-5(2,4-difluorophenyl)-1-pentene

To a stirred suspension of magnesium turnings (16.9 gm) in dry diethyl ether (1.5L) was added (argon atmosphere) a crystal of iodine and 4-bromobutene (2 ml). Soon after the reaction was initiated the remaining 4-bromobutene (101 gm) in dry diethyl ether (500 mL) was added at such a rate to maintain gentle reflux. After complete addition, the mixture was heated to reflux for 1 hour. 2,4-Difluorobenzaldehyde (100 gm) in dry diethyl ether (400 mL) was then added dropwise with a gentle reflux. The mixture was now heated for 2 hours and allowed to cool to room temperature. The entire contents of the flask were poured on 6L ice-water containing 200 ml concentrated HCl. The organic phase was separated, washed with water, saturated $NaHCO_3$, water and dried ($Na_2SO_4$). Removal of ether in vacuo provided crude 5-hydroxy-5-(2,4-difluorophenyl)pentene as an oil (136.5 gm) which was used in the next step.

b. 1-(2', 4'-Difluorophenyl)-4-penten-1-one

A solution of the product from Step a (136 gm) in glacial acetic acid (200 mL) was stirred and cooled in an ice bath to about 15° C. Chromium trioxide (144 gm) dissolved in water (160 mL) was added at such a rate to keep the temperature between 45°–50° C. After the addition was completed, the mixture was stirred at room temperature for 2 hours and then poured into 5L ice-water and extracted with diethylether (1500 ml×2). The ether extract was treated as in Step a to provide the crude 2',4'-difluorophenyl-(3-butenyl) ketone as a pale yellow oil which was chromatographed on silica gel (900 gm) using 20% methylene chloride in n-hexanes as eluent Some of the fractions which contained the desired 1-(2', 4'-difluorophenyl)-4-penten-1-one were evaporated in vacuo to provide the pure material (82 gm). This was used in the next step.

c. 2-(2', 4'-Difluorophenyl)-2-(3-propen-1-yl) oxirane

A solution of trimethylsulfoxonium iodide (184 gm) in dry DMSO (800 ml) was treated with stirring ($N_2$ atmosphere) with NaH (36.7 gr; 60% oil dispersion) in such a manner so as to avoid extensive foaming. The mixture was then stirred at room temperature for 2 hours. A solution of the ketone from Step b (82 gm) was then added at once and the mixture was heated to 50° C. After 2 hours of heating, the reaction was cooled to room temperature, poured into 6L ice-water and extracted with diethyl ether (2L×2). The ether extract was treated as in Step a to provide the crude product as an oil (74.7 gm) which was then chromatographed on silica gel (1200 gm) using n-hexane as eluent. The fractions containing the desired product were combined and evaporated in vacuo to provide pure oxirane as a light oil (36 gm). This was used immediately in the next step.

d. 1-(2',4'-Difluorophenyl)-1-[(1H-1,2,4-triazol-1-yl)methyl]4-penten-1-ol

To a suspension of sodium triazole (35 gm) in dry DMF (250 ml) was added with stirring ($N_2$ atmosphere) a solution of the oxirane from Step c (36 gm) in dry DMF (250 ml) within 10 min. The mixture was heated to 80°–85° C. and stirred overnight at this temperature. After cooling to room temperature the reaction was poured onto 4L ice-water and extracted with three 2L volumes of diethyl ether. The ether extract was treated as in Step a to provide a brown oil which was chromatographed on silica gel (1200 gm) using $CH_2Cl_2$ as eluent. Fractions containing the desired product were combined and evaporated in vacuo to provide pure 1-(2,4-difluorophenyl)-5-[(1H-1,2,4-triazol-1-yl)methyl]-4-penten-1-ol as a gum (34.2 gm). This was used in the next step.

e. 1-(2', 4'-Difluorophenyl)-1-(2-oxiranylethyl)-2[(1H-1,2,4-triazol-1-yl]ethanol A solution of product of step d (34.2 gm) in methylene chloride (950 ml) was cooled in an ice-MeOH bath. To this solution was added with stirring m-chloroperbenzoic acid (24 gm) within 15 min. The reaction mixture was then allowed to warm up to room temperature and stirred overnight. TLC indicated presence of some unreacted starting material so additional m-chloroperbenzoic acid (5 gm) was introduced and stirring continued for another 5 hours. The reaction was treated according to the procedure of Step a to provide almost pure above-named ethanol (36 gm) which was used as such in the next reaction.

f. (±)-cis- and (±)-trans-5-(2',4'-Difluorophenyl)-tetrahydro-5-[(1H-1,2,4-triazol-1-yl)methyl]-2-furanmethanol To a solution of the compound of Step e (36 gm) in methylene chloride (1500 mL) was added with stirring p-toluene sulfonic acid (23.1 gm) and the so formed mixture stirred for 72 hours. The mixture was washed with saturated Na₂CO₃ (300 ml), brine (300 ml) then dried (Na₂SO₄). Evaporation of the solvent in vacuo provided a virtually pure mixture of cis- and trans-isomers (35.5 gm). The isomers were separated on silica gel (5 kg) using 2% methanol in methylene chloride (containing 2 ml conc. NH₄OH per liter of solution) as eluent. Fractions containing the pure (±)-cis- and (±)-trans-isomers of the title compound were combined to give 10.8 gm of the less polar cis-isomer, m.p. 114°–116° C., and 10.2 gm of the more polar trans-isomer, m.p. 93°–96° C.

EXAMPLE 30

(±)-cis-5-(2,4-Difluorophenyl)tetrahydro-5-[(1H-1,2,4-triazol-1-yl)methyl]2-furanmethanol, methanesulfonate A solution of 5.91 g (20.0 mmole) of (±)-cis-5-(2,4-difluorophenyl)-5-[(1H-1,2,4-triazol-1-yl)methyl]-2-furanmethanol in 100 mL of pyridine was cooled to 0°–5° C. and 1.93 ml (25.0 mmole) of methanesulfonyl chloride was added. The so formed reaction mixture was stirred at 0°–5° C. for 3 hours. The pyridine was removed under high vac. The residue was dissolved in 500 mL of H₂CCl₂ and the so formed solution was extracted with 250 mL of 5% NaHCO₃ followed by 250 mL of H₂O. The organic phase was dried over anhydrous MgSO₄ and concentrated to give 7.19 g of the title compound, M/e, M+374.

EXAMPLE 31

(±)-cis-1-[4-[[2-(2,4-Difluorophenyl)tetrahydro-2-[(1H-1,2,4-triazol-1-yl)methyl]5-furanyl]methoxy]phenyl]-4-(1-methylethyl)piperazine A suspension of 4.24 g (19.3 mmole) of 1-methylethyl-4-(4-hydroxyphenyl)piperazine and 0.85 g (21.2 mmole) of NaH (60% oil dispersion) was stirred at room temperature for 1 hour. 7.19 g (19.3 mmole) of the title compound of Example 30 dissolved in 50 ml of DMSO, was added thereto over 10 min. The reaction mixture was stirred at 75° C. for 3 hours, cooled to room temperature and then poured the reaction mixture into 1 liter of methylene chloride. The organic phase was extracted with three 1 liter portions of H₂O, dried over anhydrous MgSO₄ and concentrated. The so formed residue was chromatographed on silica gel, eluting with 1% MeOH/H₂CCl₂ containing 1 mL conc. NH₄OH per liter of solution to give 6.3 g of solid which was treated with charcoal and recrystallized from hexane/H₂CCl₂ to give 3.20 g of the title compound as a solid, m.p. 108°–110° C. M/e, M+498; theory 65.17%C, 6.68%H, 14.08%N, 7.64%F; found 64.96%C, 6.68%H, 13.93%N, 7.51%F.

EXAMPLE 32

4-Bromo-2-butyn-1-ol, benzoate

A solution of 5.52 g (29.0 mmole) of 1-benzoxy-4-hydroxy-2-butyne in 150 mL of H₂CCl₂ was cooled to 0°–5° C. 14.4 g (43.5 mmole) of carbon tetrabromide and 12.6 g (47.8 mmole) of triphenylphosphine was added thereto. The so formed mixture was stirred for 1 hour at 0°–5° C. and then 18 hours at room temperature. The reaction mixture was concentrated to about 50 ml and poured into 1 liter of petroleum ether, and the so formed mixture was stirred for 15 min. The insoluble material and the petroleum ether was concentrated to give an oil which was chromatographed on silica gel, eluting with petroleum ether to give 7.90 g of the title compound, M/e, M+254.

EXAMPLE 33

4-[4-(1-methylethyl)-1-piperazinyl]-2-butyn-1-ol, benzoate 4.29 g (21.3 mmole) of 1-methylethylpiperazine dihydrochloride, 5.40 g (21.3 mmole) of the title compound of Example 32 and 8.83 g (63.9 mmole) of potassium carbonate in 100 mL of DMF, were stirred under Ar, at 80° C. for 1 hour. The DMF was evaporated off under high vacuum. The residue was dissolved in 500 mL of H₂CCl₂ and 500 mL of H₂O and stirred for 5 minutes. The organic phase was separated and washed with another 500 mL of H₂O and dried over anhydrous MgSO₄ and concentrated to a gum. The gum was chromatographed on silica gel, eluting with 1% MeOH/H₂CCl₂ containing 1 mL of conc. NH₄OH per liter of solution to give 2.69 g of the title compound, M/e, M+301.

EXAMPLE 34

4-[4-(1-methylethyl)-1-piperazinyl]-2-butyn-1-ol

A solution of 2.69 g (8.95 mmole) of the title compound of Example 33 in 100 ml of MeOH and 30 mL of 1N NaOH was heated at reflux for 1 hour. The MeOH was removed under vacuum and the aqueous residue stirred in 500 mL of H₂CCl₂ and 200 mL of brine. The organic phase was separated and dried over anhydrous MgSO₄ and concentrated to give 1.61 g of the title compound, M/e, M+197.

EXAMPLE 35

(±)-cis-1-[4-[[2-(2,4-Dichlorophenyl)tetrahydro-2-[(1H-1,2,4-triazol-1-yl)methyl]-5-furanyl]methoxy]-2-butynyl]-4(1-methylethyl)piperazine To a solution of 435 mg (2.21 mmole) of the title compound of Example 34 in 10 ml of DMSO, under Ar was added 98.4 mg of NaH (60% oil dispersion) and the so formed mixture was stirred for 30 min. at room temperature. 1.00 g (2.46 mmole) of the title compound of Example 3 was added and the so formed mixture stirred for 1 hour at 50° C. The reaction mixture was poured into 250 mL of H₂CCl₂ and extracted with two 250 mL portions of H₂O. The organic phase was dried over anhydrous MgSO₄ and concentrated to a gum. The gum was chromatographed on silica gel, eluting with 1% MeOH/H₂CCl₂ containing 1 ml of con. NH₄OH per liter of solution to give 907 mg of the title compound, M/e, M+506.

(±)-cis-4-[[4-[[2-(2,4-Dichlorophenyl)tetrahydro-2-
[(1H-1,2,4-triazol-1-yl)
methyl]-5-furanyl]methoxy]-2,5-dimethylphenyl]me-
thylmorpholine and
(±)-cis-4-[[2-[[2-(2,4-dichlorophenyl)tetrahydro-2[(1H-
1,2,4-triazol-1-yl)
methyl]-5-furanyl]methoxy-3,6-dimethylphenyl]me-
thyl]morpholine To a solution of 492 mg (1.78 mmole) a mixture of 2,5-dimethyl-4-(morpholinomethyl)phenol hydrochloride monohydrate and 3,6-dimethyl-2-(morpholinomethyl)phenol hydrochloride monohydrate in 10 mL of DMSO was added 342 mg (7.12 mmole) of NaH (50% dispersion) and the so formed mixture was stirred the mixture at room temperature for 30 minutes. 600 mg (1.48 mmole) of (±) cis 5-(b 2,4-dichlorophenyl)tetrahydro-5-[(1H-1,2,4-triazol-1-yl)methyl]furanmethanol methanesulfonate (from Example 3) was added and the so formed mixture stirred at 75° C. for 5 hours. The mixture was poured into 500 mL of $H_2CCl_2$ and washed with three 500 mL portions of $H_2O$. The organic phase was dried over anhydrous $MgSO_4$ and concentrated to a gum. The gum was chromatographed on silica gel, eluting with 1% $MeOH/H_2CCl_2$ containing 1 ml of con. $NH_4OH$ per liter of solution to give 270 mg of (±)-cis 4-[[4-[[2-(2,4-dichlorophenyl)tetrahydro-2-[[1H-1,2,4-triazol-1-yl)methyl-5-furanyl]methoxy]-2,5-dimethylphenyl]methylmorpholine, M/e, M+532 and 280 mg of (±)-cis 4-[[2-[[2-(2,4-dichlorophenyl)tetrahydro-2-[(1H-1,2,4-triazol-1-yl)methyl]-5-furanyl]methoxy-3,6-dimethylphenyl]methylmorpholine, M/e, M+532.

EXAMPLE 37

1-(3'-Buten-1yl)-1-(2',4'-dichlorophenyl)-2-(1H-1-imidazol-1-yl)ethanol

A mixture of 2-(2',4'-dichlorophenyl)-2-(3'-buten-1-yl)oxirane (13.5 g, 55.5 mmole), imidazole (7.6 g, 111 mmole) and $K_2CO_3$ (11.5 g, 83.2 mmole) in DMF (150 mL) was heated at 120° C. overnight. The reaction mixture was evaporated to dryness. The so formed residue was extracted with methylene chloride. The solution was washed with water, dried over $MgSO_4$ and solvent was evaporated to give 11.88 g of the title compound as a gum, M/e, M+312.

EXAMPLE 38

1-(2',4'-Dichlorophenyl)-1-(2'-oxiranylethyl)
-2-[(1H-imidazolyl-1-yl)ethanol

A solution of the title compound of Example 37 (11.88 g, 37.9 mmole) in methylene chloride (150 mL), was cooled solution to 0°–5° C. and m-chloroperbenzoic acid (13.14 g, 76.32 mmole) was added and the so formed mixture stirred overnight at room temperature. The reaction mixture was stirred with 10% sodium bicarbonate (200 ml) for ½ hour and the organic layer was evaporated and washed with water. The organic layer was dried over $MgSO_4$ and solvent evaporated to give the title compound as a gum (10.29 g), M/e, M+328.

EXAMPLE 39

(±)-cis-5-(2,4-Dichlorophenyl)tetrahydro-5-[(1H-imidazol-1-yl)methyl)-2-furanmethanol A mixture of of the title compound of Example 38 (10.0 g, 30.86 mmole) and p-toluenesulfonic acid (9.59 g, 50.41 mmole) in methylene chloride (150 ml) was stirred overnight. The reaction mixture was washed with 5% aq. sodium bicarbonate (100 ml) and water. The organic phase was dried over $MgSO_4$ and evaporated to dryness to give a gum which upon chromatography on a silica gel column, eluting with chloroform/1.5% methanol gave the title compound as a crystalline solid, 0.712 g, m.p. 311° C. M/e, M+328.

EXAMPLE 40

(±)-cis-5-(2,4-Dichlorophenyl)tetrahydro-5-[(1H-imidazol-1-yl)methyl]2-furanmethanol, methanesulfonate A solution of 1.28 g (3.9 mmole) of the title compound of Example 39 in 25 ml of pyridine was cooled to 0°–5° C. and 0.38 ml (4.89 mmole) of methanesulfonyl chloride was added and the so formed mixture stirred for 3 hours at 0°–5° C. The pyridine was removed under high vac. The residue was dissolved in 500 mL $CH_2Cl_2$ and the so formed solution extracted with 250 mL of 5% aq. $NaHCO_3$ followed by 250 mL of $H_2O$. The organic phase was dried over $MgSO_4$ and concentrated to give 1.5 g the title compound as a gum, M/e, M+406.

EXAMPLE 41

(±)-cis-1-Acetyl-[4-[4-[[2-(2,4-dichlorophenyl)-tetrahydro-2-[(1H-imidazol-1-yl)methyl]-5-furanyl]methoxy]-phenyl]piperazine A suspension of 0.19 g (0.86 mmole) of 1-acetyl-4-(4'-hydroxyphenyl)piperazine and 0.023 g (0.95 mmole) of NaH in 10 mL of DMSO was stirred at room temperature for one hour. Added 0.328 g (0.8 mmole) of the title compound of Example 40, dissolved in 10 ml of DMSO was added and the so formed mixture stirred at 75° C. for 3 hours. The reaction mixture was poured into 250 mL of $CH_2Cl_2$ and the so formed solution was extracted with three 250 ml portions of $H_2O$. The organic phase was dried over $MgSO_4$ and concentrated to a gum which was chromatographed on silica gel column eluting with 2% $MeOH/CH_2Cl_2$ containing 2 mL of conc. $NH_4OH$ per liter of solution to give 0.34 g of the title compound as a gum, M/e, M+531.

EXAMPLE 42

(±)-cis-1
[[2-(2,4-Dichlorophenyl)-tetrahydro-4-[nitrophenoxy)-methyl]-2-furanyl-1H-1,2,4-triazole Sodium hydride (135 mg; 60% oil dispersion) was added portionwise to a solution of the title compound of Example 39 (1.0 g) in DMF (15 mL). The reaction mixture was heated for 30 minutes at 45° C. and was then allowed to cool to room temperature. 1-Chloro-4-nitrobenzene (510 mg) was added in portions and the so formed mixture was stirred at room temperature. Water (120 mL) was carefully added and the so formed mixture was extracted with ethyl acetate (100 ml×2). The ethyl acetate extracts were washed once with water, dried ($MgSO_4$) and evaporated to dryness to provide a solid which was recrystallized from ether acetate/n-hexanes to give the title compound (670 mg), m.p. 161°–163°. Elemental analysis: C, 53.31; H, 3.88; N, 12.40; $C_{20}H_{18}N_4O_4Cl_2$ requires: C, 53.46; H, 4.05; N, 12.46.

EXAMPLE 43

(±)-cis-4-[[2-(2,4-Dichlorophenyl)-tetrahydro-2-[(1H-1,2,4-triazol-1-yl)methyl]-4-furanyl]methoxy]-benzenamine A solution of 3.8 g of the title compound of Example 42 (170 mL) was hydrogenated in a Paar shaker at hydrogen pressure of 27 p.s.i. in the presence of 5% Pd/C catalyst (400 mg) for 7 hours. The catalyst was removed in vacuo, and the so-formed solution washed with methylene chloride and the combined filtrates evaporated to dryness to provide the title compound as a homogenous product (3.7 g). A 70 mg portion of this product was converted to hydrochloride salt with ethereal HCl and recrystallized from ethyl acetate/methanol.

Elemental analysis: C, 48.82; H, 4.48; N, 11.31; $C_{20}H_{20}N_4O_2Cl_2HCl$ requires: C, 48.80; H, 4.10; N, 11.38

The remaining hydrochloride salt product was used without any further purification in the preparation of Example 44.

EXAMPLE 44

(±)-cis-1-[4-[[2-(2,4-Dichlorophenyl)tetrahydro-2-[(1H-1,2,4triazol-1-yl)methyl ]-5-furanyl]methoxy]phenyl]piperazine A mixture of 3.7 gm of the title compound of Example 43, 1.58 gm di-(2-chloroethyl)amine hydrochloride and 1.2 g potassium carbonate in 60 mL of butoxyethanol was refluxed for 3½ hours. The solvent was removed in vacuo at 40°–45° C., and the residue partitioned between ethyl acetate (300 mL) and water (100 mL). The so formed mixture was shaken and the two phase separated. The aqueous phase was extracted again with ethyl acetate, the organic phase dried ($Na_2SO_4$) and evaporated to dryness in vacuo. Chromatography of the residue on silica gel (200 mL) using 4% methanol 0.1% $NH_4OH$ in methylene chloride provided in some of the fractions pure title compound (180 mg). The title compound was characterized as its N-acetyl and N-isopropyl derivatives.

EXAMPLE 45

(±)-cis-3-[[[2-(2,4-Dichlorophenyl)tetrahydro-2-[(1H-1,2,4triazol-1-yl)methyl ]-5-furanyl]methoxy]methyl]pyridine To a solution of (±)cis-isomer of the title compound of Example 2 (0.820 g, 2.5 m.mole) in 25 mL dry DMSO, NaH (0.161 g, 6.71 m.mole) was added. The mixture was stirred at room temperature for one hour. Then 3-picolyl chloride hydrochloride (0.6 g, 3.6 m.mole) was added and the mixture was stirred at room temperature overnight. The mixture was diluted with 300 mL $CH_2Cl_2$ and the so formed solution washed with water several times. The organic phase was dried over $MgSO_4$. Evaporation of solvent gave gum which upon silica gel chromatography, eluting with 2% MeOH/EtOAc/ containing 0.2 mL of $NH_4OH$ gave 0.251 g of the title compound as gum, M/e, M+420

EXAMPLE 46

(±)-cis-2-[[2-(2,4-Dichlorophenyl)tetrahydro-2-[(1H-1,2,4triazol-1-yl)methyl]-5-furanyl]-methyl-5-nitropyridine To a solution of (±)-cis-isomer of the title compound of Example 2 (1.969 g, 6 m.mole) in 25 ml dry DMSO, NaH (0.158 g, 6.6 m.mole) was added at 10° to 15° C. The mixture was stirred at room temperature for 1 hr. A solution of 2-chloro-5-nitro pyridine (1.189 g, 7.0 m.mole) in 25 ml dry DMSO was added dropwise at 10° to 15° C. The mixture was stirred at room temperature overnight. The mixture was diluted with 500 ml EtOAc and washed with saturated NaCl solution several times. The organic phase was dried over $MgSO_4$. Evaporation of solvent gum which upon silica gel chromatography, eluting with methylene chloride/methanol 0.5% (v/v) gave 2.3 g of the title compound as solid, M/e, M+451.

EXAMPLE 47

(±)-cis-1H-1,2,4-Triazole, 1-[[5-[[(5-chloro-3-methyl-1-phenyl-1H-pyrazol-4-yl)methoxy]methyl]-2-(2,4-dichlorophenyl)tetrahydro-2-furanyl]methyl]

To a solution of the (±) cis-isomer of the title compound of Example 2 (0.328 g, 1 m.mole) in 5.0 ml dry DMSO, NaH (0.0264 g, 1.1 m.mole) was added. The mixture was stirred at room temperature for 1 hour. Then a solution of 5-chloro-4-chloromethyl-3-methyl-1-phenylpyrazol (0.301 g, 1.25 m.mole) in 5.0 ml dry DMSO was added dropwise and the so formed mixture was stirred at room temperature overnight. The mixture was diluted with 250 ml $CH_2Cl_2$ and was washed with $H_2O$ several times. The organic phase dried over $MgSO_4$. Evaporation of solvent gave gum which upon silica gel chromatography, eluting with methylene chloride/methanol 1% (v/v) containing 0.1 mL of $NH_4OH$ gave the title compound as a gum 0.427 g, M/e, M+533.

EXAMPLE 48

(±)-cis-5-(2,4-Dichlorophenyl)tetrahydro-5-[(1H-1,2,4-triazol-1-yl)methyl]-2-furancarboxaldehyde, oxime To a solution of the (±)-cis isomer of the title compound of Example 2 (0.984 g, 3 m.mole) in 25 ml dry DMSO, 1-ethyl-3-(3-dimethylaminopropyl)carbodiimide hydrochloride (3.45 g, 18 m.mole) was added and the suspension was stirred at room temperature for a few minutes. Then pyridine (1.5 mL, 18.6 m.mole) was added followed by trifluoroacetic acid (0.385 ml, 5 mmole). The pH of the reaction mixture was adjusted above pH 7 by adding pyridine dropwise. While stirred at room temperature, after about ½ hour reaction mixture turned into a clear solution. The clear mixture was stirred at room temperature for 5 hours.

After five hours, hydroxylamine hydrochloride (0.521 g, 7.5 m.mole) and pyridine (1 mL) were added. The reaction mixture was stirred at room temperature over the weekend.

The mixture was diluted with 400 mL of $CH_2Cl_2$ and the organic phase washed with water several times. The organic phase was dried over $MgSO_4$. Evaporation of solvent gave gum which upon silica gel chromatography, eluting with methylene chloride/methanol/0.1 ml of $NH_4OH$ gave 0.520 g of isomer-1 and 0.190 of isomer-2 of the title compound, M/e, M+342.

EXAMPLE 49

(±)-cis-[2-(2,4-Dichlorophenyl)tetrahydro-2-[(1H-1,2,4-triazol-1-yl)methyl]-5-furanyl]carbamate To a solution of 750 mg (2.29 mmole) of (±) cis isomer of the title compound of Example 2, in 20 mL of dry THF was added 0.5 ml (3.59 mmole) of triethylamine and cooled to 0°–5° C. 507 mg (2.51 mmole) of 4-nitrophenyl chloroformate was added and the so formed reaction mixture stirred at 0°-5° C. for 18 hours. An additional 0.5 ml (3.59 mmole) of triethylamine and 507 mg (2.51 mmole) of 4-nitrophenyl chloroformate were added and the so formed mixture was stirred for 4 hours at 0°-5° C. The insoluble triethylamine hydrochloride was removed by filtration and $NH_3$/MeOH was added dropwise until the pH of the mixture was 8. The so formed residue was evaporated to dryness and was chromatographed on silica gel, eluting with 1% MeOH/$H_2CCl_2$ to give 574 mg of the title compound, M/e M+372.

EXAMPLE 50

(±) cis-4-[[2-(2,4-Dichlorophenyl)tetrahydro-2-[(1H-1,2,4-triazol-1-yl)methyl]-b 5-furanyl]methyl]-2,6-dimethyl morpholine A mixture of the title compound of Example 3 (0.56 g), 2,6-dimethylmorpholine (0.8 g) and triethylamine (0.28 g) was refluxed in toluene (20 ml) for 4 days. The reaction mixture was evaporated to dryness in vacuo and the residue extracted into methylene chloride. After washing with water, the methylene chloride extract was dried ($Na_2SO_4$) and evaporated to dryness in vacuo. The residue so obtained was chromatographed over silica gel (using $CH_2Cl_2$/1.5% MeOH as eluent) to provide in some of the fractions the title compound (238 mgs), as a gum m/e, M+424.

EXAMPLE 51

(±) cis-4-[[4-[[2-(2,4-Dichlorophenyl)tetrahydro-2-[(1H-1,2,4-triazol-1-yl) methyl]-5-furanyl]methoxy]phenyl]methyl]thiomorpholine To a solution of 4-(tetrahydro-4H-1,4-thiazin-4-yl)phenol (prepared according to European Patent Application 0173258) (1.69 g) in dry DMSO (100 ml) was added NaH (0.525 g). After stirring for 30 minutes, a solution of (±) cis-5-(2,4-dichlorophenyl)tetrahydro-5-[(1H-1,2,4-triazol-1-yl)methyl]-2-furanmethanol mesylate (3.52 g) in dry dimethylsulfoxide (50 ml) was added. The reaction mixture was heated to 75° and kept at this temperature (while stirring) for 1 hour. After cooling, the reaction mixture was poured into methylene chloride (1L) and the organic phase washed with 3×1L water. The methylene chloride phase was dried ($MgSO_4$) and evaporated to dryness in-vacuo to provide a gun. which was chromatographed on a silica gel column. Elution with methylene chloride/methanol (0.5%) gave in some of the fractions the pure title compound (2.09 g) as a tan solid, m.p. 144°-145° C., m/e, M 506.

EXAMPLE 52

(±) cis-4-[[4-[[2-(2,4-Dichlorophenyl)tetrahydro-2-[(1H-1,2,4-triazol-1-yl)methyl]-5-furanyl]methoxy]phenyl]methyl]thiomorpholine-S,S-dioxide To a solution of 4-(tetrahydro-4H-1,4-thiazin-4-yl-4,4-dioxide)phenol (prepared according to European Patent Application 0173258) (0.62 g) in dry DMSO (10 ml) was added with stirring NaH (0.12 g). After stirring for 30 minutes, a solution of (±) cis-5-(2,4-Dichlorophenyl)tetrahydro-5-[(1H-1,2,4-triazol-1-yl)methyl]-2-furanmethanol mesylate (1.11 g) in dry dimethylsulfoxide (10 ml) was added. The reaction mixture was heated to 70° for 1 hour. After cooling the mixture was poured into methylene chloride and extracted with 2×500 ml water. The methylene chloride phase was dried ($MgSO_4$) and evaporated to dryness in vacuo to provide the crude product. This was chromatographed on a silica gel column using methylene chloride/methanol (0.5%) as eluent. Some of the fractions provided the pure title compound (0.8 g) m/e, (M++1) 522.

EXAMPLE 53

Dimethyl 1-(4-chlorophenyl)-7-oxabicyclo[2.2.1]hepta-2,5-diene-2,3-dicarboxylate A mixture of 2-(4-chlorophenyl)furan (prepared according to A.W. Johnson, J. of Chem. Soc. 1946, p 895-99) (0.105 g), and dimethyl acetylenedicarboxylate (0.07 mL) in distilled water (0.25 mL) was placed in a closed vial and subjected to ultrasonic vibration overnight. The reaction temperature at the end of the reaction was between 40 and 50° C. After cooling the Diels-Alder adduct was isolated by extraction with ethyl acetate. The ethyl acetate extract was dried ($Na_2SO_4$) and evaporated to dryness in-vacuo to provide almost pure product which was further purified by chromatography on silica gel using 5-10% acetone in n-hexane. The title compound (0.16 g) m.p. 84° C. was isolated from some of the combined fractions: PMR $\delta_H$ ($CDCl_3$): 3.7(s,3H), 3.84 (s, 3H), 5.76 (d, 1H, J=1.2Hz), 7.58-7.29 (m, 5H).

EXAMPLE 54

Dimethyl 1-(4-chlorophenyl)-7-oxabicyclo[2.2.1]hept-2-ene-2,3-dicarboxylate 2-(4-Chlorophenyl)furan (2.3 g) and dimethyl acetylenedicarboxylate (1.54 ml) were subjected to Diels-Alder reaction in water (5.48 ml) as described in Example 53. The resulting adduct was dissolved in EtOAc (140 ml) and hydrogenated over Adam's platinum catalyst (100 mg) at room temperature and atmospheric pressure. The uptake of one equivalent of $H_2$ required about 3 hours. The catalyst was removed by filtration and the solvent removed in-vacuo to provide a gummy product which was chromatographed over silica gel column. Elution of column with 10% acetone in n-hexane gave fractions containing the pure title compound (3.25 g) as colorless crystals:m.p. 90°-91° C.; PMR $\delta_H$($CDCl_3$): 1.55-1.7 (n,1H), 2-2.3 (m,3H), 3.62 (s,3H), 3.79(s,3H), 5.37 (d, 1H, J=4.2 Hz), 7.3-7.44 (m,4H).

EXAMPLE 55

(±) cis-2-(4-Chlorophenyl)tetrahydro-2,5-furandicarboxylic acid (i) A solution of the dimethyl ester from Example 54 (2 g) in tetrahydrofuran (13 ml) was treated with aqueous sodium hydroxide (0.25 m; 0.73 ml) at room temperature. After stirring for 18 hours, the pH of the solution was adjusted with concentrated hydrochloric acid to equal 2 and the aqueous phase extracted with ethyl acetate (3×20 ml). The combined organic extract was dried ($Na_2SO_4$) and evaporated to dryness in-vacuo to provide a brownish gummy product (1.87 g) which was used as such in the next step.

(ii) A solution of the product of step i (1.87 g) in methanol: $CH_2Cl_2$ (1:1; 30 ml) was cooled to −60° C. Ozone was passed through this stirred solution until formation of a persistent blue colour (indicating excess ozone). Argon was bubbled through the reaction mixture until the blue colour disappeared. Dimethyl sulfide (0.6 ml) was then added. The reaction mixture was stirred at −10° C. for 1 hour and finally at room temperature for 1 hour. After evaporation of the solvent in-vacuo, the residue was treated with 40% aqueous NaOH (2 ml) and 30% $H_2O_2$ (1.6 ml) while cooling in ice-salt bath. The reaction mixture was allowed to warm to room temperature and stirred for about 10 hours. With cooling (ice bath) the pH of the solution was brought to 2 by cautious addition of 6NHCl and the aqueous phase extracted with ethyl acetate (3×15 ml). The combined organic extract was dried ($Na_2SO_4$) and evaporated in-vacuo to yield the title compound as a light yellow gum (1.35 g). PMR $\delta_H$(CDCl$_3$): 2.1–2.5 (m,1H), 2.75–2.87 (m,1H), 4.82 (t,1H), 7.31–7.52 (m,4H). The title compound was used in the next reaction without further purification.

EXAMPLE 56

(±)-cis-Dimethyl-2-(4-chlorophenyl)tetrahydro-2,5-furandicarboxylate

A solution of the title compound from Example 55 (1.35 g) in methanol (50 ml) was treated with ethereal diazomethane until yellow color persisted. The solution was carefully evaporated in-vacuo and the residue was chromatographed over silica gel. Elution with 20% acetone in n-hexane gave in some of the fractions pure title compound (1.09 g) as a light yellow oil. PMR (CDCl$_3$)$\delta_H$: 2.1–2.3 (n,3H), 2.8–3 (m,1H), 3.73 (s,3H), 3.76 (s,3H), 4.75 (t,1H), 7.28–7.46 (m,4H).

EXAMPLE 57

(±)-cis-2-(4-Chlorophenyl)tetrahydro-2,5-furandimethanol

To a stirred suspension of lithium aluminium hydride (0.31 g) in dry Et$_2$O (40 ml) was added the dimethyl ester (1 g) from Example 56 in dry ether (20 ml) with cooling (ice bath). After stirring for 4 hours at room temperature the reaction was treated by successive addition of water (0.32 g), 15% NaOH (0.32 g) and water (1 g). After an additional 20 minutes, a granular precipitate separated which was removed by filtration and washed with EtOAc (50 ml) and methylene chloride (50 ml). The combined filtrates and washings were dried (Na$_2$SO$_4$) and evaporated in-vacuo to provide the title compound (0.78 g) as a crystalline solid m.p. 85°–87° C. PMR $\delta_H$(CDCl$_3$): 1.8–2.15 (m,2H), 2.23–2.63 (m,2H), 3.6–3.7 (m,2H), 3.87–3.94 (m,2H), 4.18–4.3 (m,1H), 7.31–7.37 (m,4H).

EXAMPLE 58

(±)-cis-2-(4-Chlorophenyl)tetrahydro-5[(phenylmethoxy)methyl]-2-furanmethanol and (±)-cis-2-(4-Chlorophenyl)tetrahydro-2[(phenylmethoxy) methyl]-5-furanmethanol A solution of the title compound of Example 57 (0.5 g) in dry DMF (4 ml) was treated with NaH (0.09 g; 60% dispersion in oil). After stirring for 30 minutes at room temperature the solution was cooled (ice bath) and a solution of benzyl bromide (0.26 ml) in dry tetrahydrofuran (1 ml) was added dropwise. The reaction mixture was allowed to warm up to room temperature and stirred overnight. Water (5 ml) was then added and the mixture was extracted with EtOAc (3×50 ml). The combined EtOAc extract was dried (Na$_2$SO$_4$) and evaporated to dryness in-vacuo to provide the product as a colourless gum. It was subjected to chromatography on 4 TLC plates (1 mm thick) using 20% acetone in n-hexane as eluent. The two monobenzyl ethers were isolated by extraction of two closely separated bands with ETOAc.

The less polar (120 mg) component was (±) cis-2-(4-chlorophenyl)tetrahydro-5-[(phenylmethoxy)methyl]-2-furanmethanol.

PMR $\delta_H$(DMSO): 1.75 (m,2H), 1.9 (m,1H), 2.3 (m,1H), 3.4 (m,2H), 3.5 (m,2H), 4.1 (m,1H), 4.55 (s,2H), 4.75 (m,1H), 7.25–7.4 (m,9H).

The more polar (170 mg) component was (±) cis-2-(4-chlorophenyl)tetrahydro-2-[(phenylmethoxy)methyl]-5furanmethanol.

PMR (DMSO): 1.75 (m,2H), 1.98 (m,1H), 2.28 (m,1H), 3.42 (m,2H), 3.5 (q,2H), 3.98 (m,1H), 4.45 (s,2H), 4.65 (m,1H), 7.15–7.93 (m,9H).

EXAMPLE 59

Dimethyl 1-(2,4-Dichlorophenyl)-7-oxabicyclo[2.2.1]hepta-2,5-diene-2,3-dicarboxylate The procedure of Example 53 was followed except an equivalent quantity of 2-(2,4-dichlorophenyl)furan (prepared according to A.W. Johnson, J. of Chem. Soc., 1946, p 895–99) was substituted for 2-(4-chlorophenyl)furan. The title compound was obtained as a crystalline solid m.p. 68°–71° C.; PMR $\delta_H$(CDcl$_3$): 3.7(s,3H), 3.84 (s,3H), 5.76 (d,1H), J=1.2Hz), 7.29–7.58 (m,5H).

EXAMPLE 60

Dimethyl 1-(2,4-Dichlorophenyl)-7-oxabicyclo[2.2.1]-hept-2-ene-2,3-dicarboxylate The title compound of Example 59 was partially reduced over Adam's platinum catalyst according to the procedure of Example 54 to provide the title compound of this Example as a crystalline solid, m.p. 78° C.

PMR $\delta_H$(CDCl$_3$): 1.65–1.78 (m,1H), 2.1–2.29 (m,2H), 2.3–2.45 (m,1H), 3.66 (s,3H), 3.8 (s,3H), 7.36 (d,1H,J=4.4 Hz), 7.27 (q,1H), 7.41 (d,1H,J=2.2Hz), 7.56 (d,1H,J=9Hz).

EXAMPLE 61

(±)-cis-2-(2,4-Dichlorophenyl)tetrahydro-2,5-furandicarboxylic acid

The title compound of Example 60 was treated according to the procedures of Example 55 to provide the title compound of this Example which was used without further purification in Example 62.

EXAMPLE 62

(±)-cis-Dimethyl-2-(2,4-dichlorophenyl)tetrahydro-2,5-furandicarboxylate

This was prepared from the above diacid of Example 61 according to the procedure of Example 56. The title compound was obtained as a low melting solid by chromatography over silica gel using as an eluent: 20% acetone in n-hexane.

PMR $\delta_H$(CDCl$_3$): 1.96 (m,1H), 2.35 (m,2H), 3.27 (m,1H), 3.71 (s,3H), 3.75 (s,3H), 4.77 (t,1H), 7.25–7.69 (m,3H).

EXAMPLE 63

Preparation of compounds of the formula

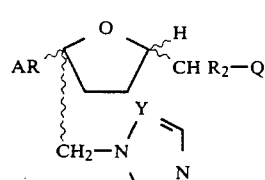

(Type i)

The title compounds of Examples 58 and 62 are treated in accordance with the procedures outlined in the lower portion of Scheme 2 to produce compounds of the above formula having Ar, Y, R₂, and Q defined as in the Table below

EXAMPLE 64

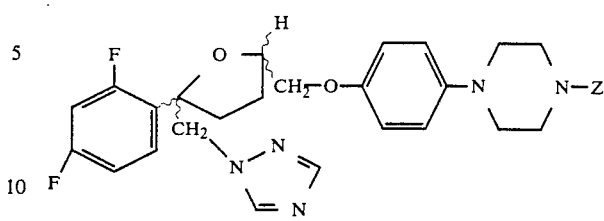

WHEREIN Z =

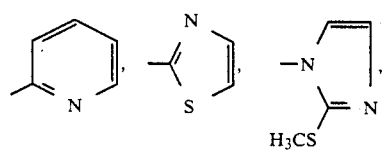

| Ar | Y | R₂ | Q |
|---|---|---|---|
| 4-ClC₆H₄— | CH | H | —O—C₆H₄—N⟩N—CH(CH₃)₂ |
| " | N | " | " |
| " | CH | CH₃ | " |
| " | N | " | " |
| 2,4-Cl₂C₆H₃— | CH | H | —O—C₆H₄—N⟩N—C₆H₄—N–C(O)–N(sec-Bu)–N=CH (triazolinone) |
| " | N | " | " |
| " | CH | CH₃ | " |
| 2,4-ClC₆H₄ | CH | H | —S—(2-pyridyl) |
| " | N | H | " |
| " | CH | C₂H₅ | " |
| " | N | " | " |
| 2,4-Cl₂C₆H₃— | N | H | —N—CH₂—C≡C—C≡C—C(CH₃)₃ |
| " | CH | " | " |
| " | N | C₂H₅ | " |
| " | CH | " | " |
| 4-ClC₆H₄ | N | H | —S—C₆H₄—N(triazole) |
| " | CH | " | " |
| " | N | C₃H₇ | " |
| " | CH | " | " |

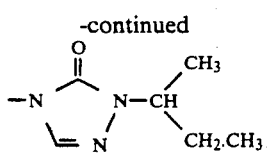

The starting material (Z=H) prepared in accordance with the procedure of Example 44 is treated in accordance with the procedure of U.S. Pat. No. 4,456,605 (columns 5 to 16) to produce compounds of the above formula.

EXAMPLE 65

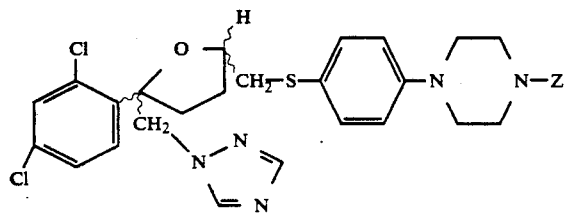

wherein Z is as defined in Example 64

The procedure of Example 25 is followed except that an equivalent quantity of p-nitrobenzenethiol is substituted for 4-(1H-1,2,4-triazol-1-yl) thiophenol. The product so formed is reduced in accordance with the procedure of Example 43 and the so-formed product is converted into the corresponding piperazine derivatives by the procedure of Example 44. The so-formed product is converted into the title compounds in accordance with the procedure of U.S. Pat. No. 4,456,605.

EXAMPLE 66

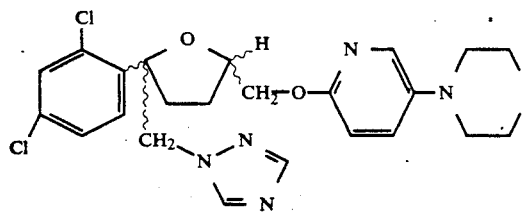

wherein Z is as defined in Example 64

The title compound of Example 46 is reduced to the corresponding amino compound in accordance with the procedure of Example 43. The so-formed product is converted into the corresponding piperazine compound in accordance with the procedure of Example 44. The so-formed piperazine compound is converted into the title compounds in accordance with the procedure of U.S. Pat. No. 4,456,605.

In a similar fashion compounds of the formula

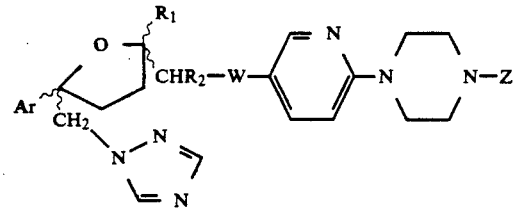

wherein Ar is phenyl substituted by one or more of halo, nitro, cyano, lower alkyl, lower alkoxy or perhalo (lower)alkyl; and A, B, C, Y, W, Z, $R_1$ and $R_2$ are defined as hereinabove (but $R_2$ is not hydroxy) may be made by substituting the appropriate starting material for the starting material used in Example 44 and thereafter using the procedure of U.S. Pat. No. 4,456,605.

EXAMPLE 67

6-[4-(1-Methylethyl)-1-piperazinyl]-3-pyridinol a) Ethyl 4-(1-methylethyl)-1-piperazinylcarboxylate A solution of ethyl 1-piperazinylcarboxylate (25.0 mL, 0.171 mole) and acetone (37.7 mL, 0.513 mole) in methanol (MeOH) (500 mL) was cooled to 0°-5° C. Sodium cyanoborohydride (10.7 g., 0.171 mole) was added in two portions. The so-formed mixture was stirred at 0°-5° C. for 8 hours while maintaining the pH at 4-6 by dropwise addition of 6N HCl. The temperature of the reaction mixture was allowed to slowly rise to RT overnight. The reaction mixture was evaporated in vacuo to provide a residue which was dissolved in $H_2CCl_2$ (500 mL) and 5% $NaHCO_3$ (500 mL). The $H_2CCl_2$ layer was separated, washed with brine (500 mL), dried over anhydrous $MgSO_4$, and evaporated in vacuo. The so-formed residue was chromatographed on silica gel, eluting with 1% MeOH/$H_2CCl_2$ (v/v) containing 1 mL of conc. $NH_4OH$ per liter of solution to give 18.9 g of the title compound of Example 67(a) as a gum, M/e, M+201.

b) 1-(1-Methylethyl)piperazine dihydrochloride

A solution of the title compound of Example 67(a) (18.9 g, 94.3 mmole) in conc. HCl (190 mL) was heated at reflux overnight. The so-formed reaction mixture was evaporated in vacuo; the remaining $H_2O$ was removed by azetroping with absolute ethanol (abs. EtOH) (3×250 mL) to give 15.5 g of the title compound of Example 67(b) as a gum M/e, M+202.

c) 1-(5-Bromo-2-pyridinyl)-4-(1-methylethyl)piperazine

A mixture of the title compound of Example 67(b) (14.3 g, 71.1 mmole), 2,5-dibromopyridine (33.7 g, 142.2 mmole) and triethylamine (49.5 mL, 0.355 mole) was stirred at 75° C. for 48 hours. The so-formed reaction mixture was evaporated in vacuo to provide a residue which was dissolved in $H_2CCl_2$ (1 liter) and 5% $Na_2CO_3$ (500 mL). The $H_2CCl_2$ layer was separated, washed with $H_2O$ (500 mL), dried over anhydrous $MgSO_4$, and evaporated in vacuo. The so-formed residue was chromatographed on silica gel, eluting with 1% MeOH/$H_2CCl_2$ (v/v) containing 1 mL of conc $NH_4OH$ to give 7.77 g of the title compound of Example 67(c) as a gum M/e, M+285.

d) 1-(5-Methoxy-2-pyridinyl)-4-(1-methylethyl)piperazine

To a solution of sodium methoxide (NaOMe), made from Na(2.76 g, 120 mmole) in MeOH (100 mL), was added dry DMF (100 ml), the title compound of Example 67(c) (8.52 g., 30.0 mmole), and cuprous iodide (5.71 g, 30.0 mmole). The so-formed mixture was heated at reflux for 48 hours, cooled to RT, and the insoluble inorganics filtered off. The filtrate was poured into $H_2CCl_2$ (1 liter) and the $H_2CCl_2$ layer was extracted with $H_2O$ (3×1 liter). The $H_2CCl_2$ layer was dried over anhydrous $MgSO_4$ and evaporated in vacuo. The so-formed residue was chromatographed on silica gel, eluting with 1% MeOH/$H_2O$ (v/v) containing 1 mL of conc $NH_4OH$ per liter of solution to give 3.55 g of the title compound of Example 67(d) as a gum, M/e, M+236.

e) 6-[4-(1-Methylethyl)-1-piperazinyl]-3-pyridinol

A solution of title compound of Example 67(d) (3.55 g, 15.1 mmole) in 47% HBr (35 ml) was heated at reflux for 6 hrs. The so-formed reaction mixture was evaporated in vacuo; the remaining H₂O was removed by forming a azeotrope with abs. EtOH (3×250 mL). The residue was dissolved in MeOH (50 ml) and MeOH/NH₃ (gas) was added dropwise until pH of the mixture was 8. The reaction mixture was evaporated in vacuo to provide a residue which was recrystallized from MeOH to give 3.35 g of the title compound of Example 67(e) as a gum M/e, M+222.

EXAMPLE 68

(+)-cis and (+)-trans-1-[4-[[2-(2,4-Difluorophenyl-2-[(1H-1,2,4-triazol-1-yl-methyl]tetrahydro-4-furanyl]methoxy]-phenyl]-4-(1-methylethyl)piperazine a) Ethyl 5-(2,4-difluorophenyl)tetrahydro-2-oxo-5[(1H-1,2,4-triazol-1-yl)methyl[3-furancarboxylate To a solution of diethyl malonate (6.4 ml, 42.2 mmole) in 50 mL of dry dimethyl sulfoxide (DMSO), NaH (60% oil dispersion, 1.69 g, 42.2 mmole) was added. After stirring the so-formed mixture for 30 min. at RT, 1-[[2-(2,4-difluorophenyl)oxiranyl]methyl]-1-H-1,2,4-triazole (5.0 g, 21.1 mmole) (described in patent GB 2099818 A) was added and the mixture stirred overnight at 50° C. Upon cooling to RT, the mixture was poured into 500 mL ethyl acetate (EtOAc) and 500 mL of brine. The organic layer was separated, washed with 500 mL of brine, dried over anhydrous MgSO₄, and evaporated in vacuo to provide a residue. The residue was chromatographed on silica gel, eluting with 50% EtOAc to give 1.5 g of the title compound as a gum, M/e M+352.

b) 4-(2,4-Difluorophenyl)-2-(hydroxymethyl)-5-(1H-1,2,4-triazol-1-yl)-1,4-pentanediol The title compound of Example 68(a) (4.8 g, 13.6 mmole) and lithium chloride (0.96 g, 27.2 ml) were dissolved in abs. EtOH (250 mL) and cooled to 0°-5° C. Sodium borohydride (1.03 g, 27.2 mmole) was added to the solution and the reaction mixture was stirred overnight and the temperature of the mixture slowly was allowed to rise to RT. Water (10 mL) was added thereto and the so-formed mixture was stirred for 30 min. at RT. The mixture was evaporated in vacuo to give a residue containing the title compound, of Example 68(b), as a gum M/E, M+314.

c) 5-(2,4-Difluorophenyl)tetrahydro-5-[(1H-1,2,4-triazol-1-yl-)methyl]-3-furanmethanol The residue from Example 68(b) was dissolved in 6N HCl (100 mL) and dioxane (100 mL). The so-formed mixture was heated at reflux overnight and then was cooled to RT and conc. NH₄OH was added until the pH of mixture was 8-9. Brine (100 mL) was added thereto and the reaction mixture was extracted with H₂CCl₂ (250 mL). The organic layer was separated, dried over anhydrous MgSO₄ and evaporated in vacuo to give a residue. The residue was chromatographed on silica gel, eluting with 2% MeOH/H₂CCl₂ containing 2 mL conc. NH₄OH per liter of solution to give 1.80 g of the title compound of Example 68(c), as a gum, M/e, M+296.

d) 5-(2,4-Difluorophenyl)tetrahydro-5-[(1H-1,2,4-triazol-1-yl)methyl]-3-furanmethanol, methanesulfonate The title compound of Example 68(c) (1.86 g, 6.30 mmole) was dissolved in dry pyridine (25 ml). The solution was cooled to 0°-5° C., methanesulfonyl chloride (0.61 mL, 7.78 mmole) was added thereto and the mixture was stirred 2 hrs. at 0°-5° C. The reaction mixture was evaporated in vacuo to provide a residue which was dissolved in H₂CCl₂ (150 mL) and 5% NaHCO₃ (50 mL). The organic layer was separated, washed with brine (50 mL), dried over anhydrous MgSO₄ and evaporated in vacuo to give 2.36 g of the title compound of Example 68(d), as a gum M/e, M+3.74.

e) (+)-cis and (+)-trans-1-[4-[[2-(2,4-Difluorophenyl)-2-[(1H-1,2,4-triazol-1 -yl)methyl]tetrahydro-4-furanyl]methoxy]phenyl]-4-(1-methylethyl)piperazine 1-(4-Hydroxyphenyl)-4-(1-methylethyl)piperazine (1.39 g, 6.30 mmole) was suspended in 20 mL of dry DMSO. 277 mg (6.93 mmole) of NaH (60% oil dispersion) was added thereto and the so-formed suspension was stirred for 30 min. at room temperature. The title compound of Example 68(d) (2.36 g, 4.30 mmole) dissolved in 10 mL of dry DMSO was added thereto and the so-formed mixture stirred at 75° C. for 1 hr.. The reaction mixture was poured into 500 mL of H₂CCl₂ and the H₂CCl₂ extracted with 2×500 mL portions of water. The organic layer was dried over anhydrous MgSO₄ and concentrated to a gum. The gum was chromatographed on silica gel, eluting with 1% MeOH/H₂CCl₂ containing 1 mL of conc. NH₄OH per liter of solution to give 400 mg of the less polar trans-isomer of title compound of Example 68(e) as a gum, M/e M+498 and 457 mg of the more polar cis-isomer of the title compound of Example 68(e) as a gum, M/e M+498.

EXAMPLE 69

(+-cis-1-[5-[[4-(2,4-Dichlorophenyl)tetrahydro-4-[(1H-1,2,4-triazoyl-1-yl)methyl -2-furanyl]methoxy-7-2-pyridenyl]-4-(1-methylethyl)-piperazine a) (±)-1-(2,4-Dichlorophenyl)-3,8-dioxabicyclo-[3,2,1]octane-2,4-dione To a solution of the crude diacid (1.5 gm) from Example 61 in dry CH₂Cl₂ (13 mL) was added ethoxyacetylene (2.5 mL). After stirring for 3 days at room temperature in a stoppered flask, the reaction mixture was evaporated to dryness under reduced pressure to provide the title compound of Example 69(a). It was used in the reaction below, without further purification.

b) (±)-1-(2,4-Dichlorophenyl)-3,8-dioxabicyclo[3,2,1]-octane-2-one

To a solution of the anhydride from Example 69(a) in tetrahydrofuran (5 ml) was added NaBH₄ (0.25 gm) with ice-bath cooling. After stirring the so-formed reaction mixture for 1 hour, dry methanol (1.5 mL) was added dropwise with cooling (ice-bath). Stirring was continued for an additional 3 hours and then the mixture was acidified to pH 1 with 6N HCl and extracted with $CH_2Cl_2$ (4×40 mL). The combined organic layers were dried ($Na_2SO_4$) and the solvent was evaporated in-vacuo. The so-formed residue was dissolved in acetone (5 mL) and kept in a freezer for 3 days. The title product of Example 69(b) separated as colorless crystalline solid, (0.7 g), m.p. 136°–137° C., and was collected by filtration: PMR $\delta_H$(CDCl$_3$): 2.03 (m,1H), 2.165 (m,1H), 2.4 (m,1H) 3.05 (m,1H), 3.72 (q,1H), 3.99 (q,1H), 4.37 (m,1H), 7.27 (q,1H), 7.4 (d,1H), 7.59 (d,1H)

c)
(±)-cis-2-(2,4-Dichlorophenyl)tetrahydro-2,5-furanedimethanol

A suspension of lithium aluminum hydride (LAH) (310 mgs) in dry diethyl ether )40 mL) was efficiently stirred under a $N_2$ atmosphere and treated dropwise with a solution of the diester of Example 62, (1 gm) in diethyl ether(20 mL). After stirring the reaction mixture at room temperature for 4 hours, water (0.32 mL) and then aqueous NaOH (320 mgs in 1 ml water) were added. The so-formed mixture was stirred for another 20 minutes. The granular precipitate so-obtained was removed by filtration and washed with EtOAc. The combined filtrate was dried ($Na_2SO_4$) and evaporated to dryness in-vacuo. The product so-obtained was purified by chromatography on silica gel using 5–25% acetone/n-hexane as solvent to provide 0.7 g of the title product of Example 69(c), as a solid, m.p. 85°–86° C.; PMR $\delta_H$(CDCl$_3$): 1.95 (m,2H), 2.3 (m,1H), 2.6 (m,3H), 3.7 (m,2H), 4.05 (m,3H), 7.22 (q,1H), 7.35 (d,1H), 7.68 (d,1H).

d)
(±)-cis-1-(2,4-Dichlorophenyl)tetrahydro-2,5-furandimethanol,5-acetate (I) and (±)-cis-2-(2,4-Dichlorophenyl)tetrahydro-2,5-furandimethanol,2-acetate (II)

To a solution of the diol of Example 69(c) (0.2 gm) in dry pyridine (0.06 mL) and methylene chloride (1.5 mL) was added 0.085 mL of acetic anhydride. After stirring for 3 hrs. at room temperature, the reaction mixture was evaporated in-vacuo and chromatographed on silica gel using 25% acetone/n-hexane as eluent to provide 0.06 g of the monoacetate (I) of Example 69(d) and 0.04 g of the monoacetate (II) of Example 69(d); PMR of (I) $\delta_H$(CDCl$_3$): 1.88 (m,2H), 2.14 (s,3H), 2.52 (m,3H), 3.67 (q,1H), 4.015 (q,1H), 4.23 (m,3H), 7.22 (q,1H), 7.63 (d,1H), 7.65 (d,1H); PMR of (II) $\delta_H$ (CDCl$_3$): 1.88 (m,2H), 2.16 (s,3H), 2.32 (m,1H), 2.32 (m,1H), 2.57 (m,2H), 3.56 (m,1H), 3.89 (m,1H), 4.12 (m,1H), 4.32 (d,1H), 4.66 (d,1H), 7.25 (q,1H), 7.37 (d,1H), 7.72 (d,1H).

e)
(±)-5-(2,4-Dichlorophenyl)tetrahydro-5-[[methylsulfenyl)oxy]methyl]-2-furanmethanol,acetate To a solution of the mono-acetate (I) of Example 69(d) 0.18 g in dry pyridine (0.054 mL) and $H_2CCl_2$ (1.5 mL) was added methane sulfonyl chloride (0.051 mL) with cooling (ice-salt bath). After stirring for 2 hours at room temperature, the reaction mixture was treated with ice water (~10 mL) and extracted with $H_2CCl_2$ (2×12 mL). The $H_2CCl_2$ extract was washed with water (~5 mL), dried ($Na_2SO_4$) and evaporated in-vacuo. The product so-obtained was chromatographed on silica gel using 20% acetone/n-hexane as eluent to provide 0.119 g of the title compound of Example 69(e) PMR $\delta_H$(CDCl$_3$): 1.89 (m,1H), 2.1 (s,3H), 2.36 (m,1H), 2.61 (m,1H), 2.96 (s,3H), 4.21 (m,3H), 4.39 (d,1H), 4.57 (d,1H), 7.26 (q,1H), 7.37 (d,1H), 7.69 (d,1H).

f)
(±)-cis-5-(2,4-Dichlorophenyl)tetrahydro-5-[(1H-1,2,4-triazol-1-yl)methyl]-2-furanmethanol To a solution of the title compound of Example 69(e) in dry DMF (0.7 mL) was added sodium triazole (0.082 g) at room temperature. The reaction mixture was heated (bath temp. 100° C.) for 24 hours. The reaction mixture was cooled and water (30 mL) was added and the mixture extracted with EtOAc (3×25 mL). The combined organic extract was evaporated in-vacuo and the so-formed residue treated with 10% aqueous NaOH (1.5 mL) and ethanol (5 mL). The mixture was warmed (bath temp. 45°) overnight and then evaporated in-vacuo to dryness. The residue so obtained was distributed between water (~5 mL) and $H_2CCl_2$ (~10 ml). The organic phase was separated and the aqueous phase extracted with more $H_2CCl_2$ (2×20 mL). The combined $H_2CCl_2$ extracts were dried ($Na_2SO_4$) and evaporated in-vacuo. Chromatography of the crude product over silica gel using 20% acetone/n-hexane followed by 5% MeOH/CHCl$_3$ provided a crystalline solid (0.042 gm), m.p. 133°–134° C., the spectral characteristics of which were identical with the cisisomer isolated from Example 2.

g)
(±)-cis-1-[5-[[4-(2,4-Dichlorophenyl)tetrahydro-4-[(1H-1,2,4-triazol-1-yl) methyl]-2-furanyl]methoxy]-2-pyridinyl]-4-(1-methylethyl)piperazine To a solution of title compound of Example 67 (1.11 g, 5.0 mmole) in dry DMSO (20 ml) was added NaH (60% oil dispursion, 240 mg, 6.0 mmole) and the so-formed reaction mixture was stirred for 20 min. A solution of cis-5-(2,4-dichlorophenyl)tetrahydro-5-[(1H-1,2,4-triazol-1-yl)methyl]-2-furanmethanol mesylate (2.10 g, 5.0 mmole) prepared from the title compound of Example 69(f) in accordance with the procedure of Example 3 in dry DMSO (20 ml) was added thereto. The mixture was stirred at 50°–60° C. for 4 hrs. After cooling to RT, the mixture was poured into $H_2CCl_2$ (500 mL) and washed with $H_2O$ (2×250 mL). The $H_2CCl_2$ layer was dried over anhydrous MgSO$_4$ and evaporated in-vacuo. The residue was chromatographed on silica gel, eluting with 2% MeOH/$H_2CCl_2$ containing 2 mL of conc. NH$_4$OH per liter of solution to give 290 mg of the title compound of Example 69, as a gum, M/e, M+532.

EXAMPLE 70

(±)-cis-[4-[[4-(2,4-Difluorophenyl)-4-[(1H-1,2,4-triazol-1-yl)methyl]tetrahydro-2-furanyl]methoxy]phenyl]-4-(1-methylethyl)piperazine a) Diethyl 2-(2,4-difluorophenyl)propanedionate

Diethyl carbonate (100 mL, 0.826 mole) and ethyl, 2,4-difluorobenzeneacetate (29.0 gm, 0.145 mole) were heated to gentle reflux. An EtOH solution of sodium ethoxide (NaOEt), made from adding Na(3.34 g, 0.145 mole) to 60 mL of abs. EtOH, was added dropwise over 1 hr. while EtOH was removed at the same rate by distillation. After addition of NaOEt was complete, the mixture was heated at reflux for 1 hr. The reaction mixture was poured into H$_2$CCl$_2$ (500 mL) and water (250 mL) and acidified to pH 1 with 6N HCl. The organic layer was separated, washed with brine (250 mL), dried over anhydrous MgSO$_4$, and evaporated in vacuo to give 41.1 g of the title compound of Example 70(a), as a gum M/e, M+2.73.

b) Diethyl 2-(2,4-difluorophenyl)-2-(2-propenyl)-propanedioate

To a solution of NaOEt, made from Na (3.67 g, 159 mole) in abs. EtOH (500 ml), was added the title compound of Example 70(a) (41.0 g, 0.145 mole). The mixture was heated to reflux, and allyl bromide (13.8 mL, 159 mole) was added dropwise thereto over a 10 min. period and the so-formed mixture was heated at reflux for 90 min. The EtOH was removed in vacuo and the resulting residue was dissolved in H$_2$CCl$_2$ (750 ml) and water (250 ml) and acidified to pH 2-3 with 6NHCl. The organic layer was separated, washed with brine, dried over anhydrous MgSO$_4$, and evaporated in vacuo to give 40.5 g of the title compound of Example 70(b), as a gum, M/e, M+313.

c) 2-(2,4-Difluorophenyl)-2-(2-propenyl)-1,3-propanediol

The title compound of Example 70b (40.5 g, 0.129 mole), in 100 mL of dry tetrahydrofuran (THF), was added dropwise over 20 min. to a stirred cooled solution (0°-5° C.) of 1.0M LAH in THF (155 mL, 1.55 mole), and so-formed reaction mixture was stirred for 2 hrs. at RT. The mixture was cooled to 0°-5° C. and water was added (15 mL) dropwise over 30 min. The so-formed reaction mixture was concentrated in vacuo to about 200 mL. The concentrate was poured into H$_2$CCl$_2$ (1 liter) and H$_2$O (200 ml) and acidified to pH 2-3 with 6N HCl. The H$_2$CCl$_2$ layer was separated, washed with brine (250 ml), dried over anhydrous MgSO$_4$, and evaporated in vacuo. The residue was chromatographed on silica gel, eluting with hexane/EtOAc (2:1) to give 16.4 g of the title compound of Example 70c, as a gum, M/e, M+229.

d) (±)-cis- and (±) trans-5-(Bromomethyl)-3-(2,4-difluorophenyl)-tetrahydro-3-furanmethanol A solution of the title compound of Example 70(c) (20.2 g, 88.5 mmole) in 250 mL of dry H$_2$CCl$_2$, was cooled to 0°-5° C. Pyridine (7.09 mL., 88.5 mmole) and bromine (4.83 mL, 88.5 mmole) were added thereto. After stirring the reaction mixture for 2 hrs. at 0°-5° C., 250 mL of H$_2$CCl$_2$ and 100 mL of H$_2$O were added. To the so-formed mixture, 10% Na$_2$SO$_3$ was added dropwise until the bromine color disappeared. The mixture was acidified to pH 2-3 with 6N HCl. The H$_2$CCl$_2$ layer was separated, washed with brine (250 mL), dried over anhydrous MgSO$_4$, and evaporated in vacuo. The so-formed residue was chromatographed on silica gel, eluting with hexane/EtOAc (3:1) to give 12.3 g of the less polar cis-isomer of the title compound of Example 70(d), M/e, M+308 and 12.9 g of the trans-isomer of the title compound of Example 70(d) as a gum, M/e, M+308.

e) (±)-cis-2-[[5-(Bromomethyl)-3-(2,4-diflurorphenyl)-tetrahydro-3-furanyl]methoxy]tetrahydro-2-H-pyran To a solution of the cis-compound of Example 70(d) (12.3 g, 40.0 mmole) in dry H$_2$CCl$_2$ (150 ml), 2,3-dihydropyran (5.5 ml, 60 mmole) and pyridinium p-toluenesulfonate (1.01 g, 4.0 mmole) were added. The mixture was stirred for 3 hrs. at RT and poured into H$_2$CCl$_2$ (500 ml and washed with H$_2$O (2×500 ml). The H$_2$CCl$_2$ layer was dried over anhydrous MgSO$_4$ and evaporated in vacuo to give 15.5 g of the title compound of Example 70(e), as a gum, M/e, M+392.

f) (±)-cis-1-[4-[[4-(2,4-Diflurorphenyl)-4-[[tetrahydro-2H-pyran-2-yl)oxy]methyl]tetrahydro-2-furanyl]-methoxy]phenyl]-4-(1-methylethyl)piperazine 1-(4-Hydroxyphenyl)-4-(1-methylethyl)piperazine (8.73 g, 39.6 mole) was suspended in 150 ml of dry DMSO. NaH (1.74 g 43.6 mmole, 60% oil dispersion) was added and the suspension so-formed was stirred for 1 hr. at RT. The title compound of Example 70(e) (15.5 g, 39.6 mmole) in 100 ml of dry DMSO was added and the so-formed mixture stirred at 60°-70° C. for 2 hrs. The mixture was poured into 2 liters of H$_2$CCl$_2$ and extracted with 2 liters of H$_2$O, followed by 2 liters of 1N NaOH, followed by 2 liters of brine. The H$_2$CCl$_2$ was dried over anhydrous MgSO$_4$ and evaporated in vacuo. The residue was chromatographed on silica gel, eluting with 2% MeOH/H$_2$CCl$_2$ containing 2 ml of conc. NH$_4$OH per liter of solution to give 4.0 g of the title compound of Example 70(f), as a gum M/e, M+531.

g) (±)-cis-3-(2,4-Difluorophenyl)tetrahydro-5-[[4-[-(1-methylethyl)-1-piperazinyl]phenoxy]methyl]-3-furanmethanol The title compound of Example 70(f) (4.00 g, 7.54 mmole) was dissolved in 25 mL of 10% HCl. The mixture was stirred at RT for 90 min. and then poured into H$_2$CCl$_2$ (500 mL) and H$_2$O (200 mL) and basified to pH 9-10 with 50% NaOH. The H$_2$CCl$_2$ layer was washed with brine (200 mL) dried over MgSO$_4$, and evaporated in vacuo. The residue was chromatographed on silica gel, eluting with 2% MeOH/H$_2$CCl$_2$ containing 2 mL of conc. NH$_4$OH per liter of solution to give 2.55 g of the title compound of Example 70(g) as a gum, M/e, M+447.

h) (±)-cis-3-(2,4-Difluorophenyl)tetrahydro-5-[[4-[4(1-methylethyl)-1-piperazinyl]phenoxy]methyl]-3-furanmethanol, methanesulfonate The title compound of Example 70(g) (2.55 g, 5.71 mmole) was dissolved in dry pyridine (25 mL). After cooling the solution to 0°-5° C., methanesulfonyl chloride (0.49 mL, 6.28 mmole) was added and the mixture was stirred 2 hrs. at 0°-5° C. The reaction mixture was evaporated in vacuo, and the residue was dissolved in H$_2$CCl$_2$ (300 mL) and 5% NaHCO$_3$ (300 mL). The H$_2$CCl$_2$ layer was separated, washed with brine (200 mL), dried over anhydrous MgSO$_4$, and evaporated in vacuo to give the title compound of Example 70(h) 3.25 g, as a gum, M/e, M+5.25.

i)

(±)-cis-1-[4-[[4-(2,4-Diflurorphenyl)-4-[(1H-1,2,4-triazol-1-yl)methyl]tetrahydro-2-furanyl]methoxy]phenyl]-4-(1-methylethyl)piperazine To a solution of the title compound of Example 70(h) (2.99 g, 5.71 mmole) in dry DMF (30 ml) was added sodium triazole (780 mg., 8.56 mmole. The mixture was stirred overnight at 90°–100° C. The mixture was cooled to RT and poured into $H_2CCl_2$ (500 ml) and extracted with $H_2O$ (3×500 ml). The $H_2CCl_2$ layer was dried over anhydrous $MgSO_4$ and evaporated in vacuo. The so-formed residue was chromatographed on silica gel, eluting with 1% MeOH/$H_2CCl_2$ containing 1 ml conc. $NH_4OH$ per liter of solution to give 1.62 of the title compound of Example 70(i), as a gum, M/e, M+498.

EXAMPLE 71

(±)-trans-1-[4-[[4-(2,4-Difluorophenyl)-4-[(1H-1,2,4-triayol-1-yl)methyl]tetrahydro-2-furanyl]methoxy]phenyl [-4-(1-methylethyl)piperazine a)

(±)-trans-2-[[5-(Bromomethyl)-3-(2,4-difluorophenyl)-tetrahydro-3-furanyl]methoxy]tetrahydro-2-H-pyran To a solution of the (±)-trans compound of Example 70(d) (12.9 g, 42.0 mmole) in dry $H_2CCl_2$ (150 ml 2,3-dihydropyran (5.75 ml, 63.0 mmole) and pyridinium p-toluenesulfonate (1.06 g, 4.2 mmole) were added. The mixture was stirred for 3 hrs. at RT and poured into $H_2CCl_2$ (500 mL). The $H_2CCl_2$ layer was washed with $H_2O$ (2×500 mL), dried over anhydrous $MgSO_4$ and evaporated in vacuo to give 16.3 g of the title compound of Example 71(a) as a gum, M/e, M+392.

b)

(±)-trans-1-[4-[[4-(2,4-Difluorophenyl)-4-[[tetrahydro-2H-pyran-2-oxy]methyl]tetrahydro-2-puranyl]methoxy]phenyl]-4-(1-methylethyl)piperazine 1-(4-Hydroxyphenyl)-4-(1-methylethyl)piperazine (9.18 g, 41.7 mmole) was suspended in 150 mL of dry DMSO. NaH (1.83 g, 45.9 mmole, 60% oil dispersion) was added and the so-formed suspension was stirred for 1 hr. at RT. The title compound of Example 71(a) (16.3 g, 41.7 mmole) in 100 mL of dry DMSO was added and the so-formed mixture stirred at 60°–70° C. for 2 hrs. The so-formed mixture was poured into 2 liters of $H_2CCl_2$ and extracted with 2 liters of $H_2O$, followed by 2 liters of 1N NaOH, followed by 2 liters of brine. The $H_2CCl_2$ solution was dried over anhydrous $MgSO_4$ and evaporated in vacuo. The so-formed residue was chromatographed on silica gel, eluting with 2% MeOH/$H_2CCl_2$ (v/v) containing 2 mL of conc. $NH_4OH$ per liter of solution to give 6.48 g of the title compound of Example 71(b), M/e, M+531 c)

(±)-trans-3-(2,4-Difluorophenyl)tetrahydro-5-[[4-[4(1-methylethyl)-1-piperazinyl]phenoxy]methyl]-3-furanmethanol The title compound of Example 71(b) (6.48 g, 12.2 mmole) was dissolved in 30 mL of 10% HCl. The mixture was stirred 90 min. at RT, poured into $H_2CCl_2$ (500 ml) and $H_2O$ (200 ml) and basified to pH 9-10 with 50% NaOH. The $H_2CCl_2$ layer was washed with brine (200 ml) dried over anhydrous $MgSO_4$, and evaporated in vacuo. The so-formed residue was chromatographed on silica gel, eluting with 1% MeOH/$H_2CCl_2$ (v/v) containing 1 ml conc. $NH_4OH$ per liter of solution to give 4.31 of the title compound of Example 71(c), as a gum, M/e, M+447.

d)

(±)-trans-3-(2,4-Difluorophenyl)tetrahydro-5-[[4-[4-(1-piperazinyl]phenoxy]methyl]-3-furanmethanol, methanesulfonate The title compound of Example 71(c) (4.31 g, 9.65 mmole) was dissolved in dry pyridine (30 mL). After cooling the so-formed mixture to 0°–5° C., methanesulfonyl chloride (0.82 mL, 10.6 mmole) was added. The so-formed mixture was stirred 2 hrs. at 0°–5° C., and then evaporated in vacuo. The so-formed residue was dissolved in $H_2CCl_2$ (300 mL) and 5% $NaHCO_3$ (200 mL). The $H_2CCl_2$ layer was separated, washed with brine (200 mL), dried over anhydrous $MgSO_4$, and evaporated in vacuo to give 5.14 g of the title compound of Example 71, as a gum, M/e, M+5.25.

e)

(±)-trans-1-[4-[[4-(2,4-Difluorophenyl)-4-[(1H-1,2,4-triayol-1-yl)methyl]tetrahydro-2-furanyl]-methoxy]phenyl]-4-(1-methylethyl)piperazine To a solution of the title compound of Example 70(d) (5.14 g, 9.65 mmole) in dry DMF (50 mL) was added sodium triazole (1.32 g, 14.5 mmole). The so-formed mixture was stirred overnight at 90°–100° C. The mixture was cooled to RT and poured into $H_2CCl_2$ (500 mL) and extracted with $H_2O$ (3×500 mL). The $H_2CCl_2$ was dried over anhydrous $MgSO_4$ and evaporated in vacuo. The so-formed residue was chromatographed on silica gel, eluting with 1% MeOH/$H_2CCl_2$ (v/v) containing 1 mL conc. $NH_4OH$ per liter of solution to give 2.43 g of the title compound of Example 71(e) as a gum, M/e, M+498.

EXAMPLE 72

(±)-trans-2-[(4-(4-Isopropylpiperazin-1-yl)-phenoxy)-methyl]-4-(2,4-dichlorophenyl)-4-[1H-1,2,4-triazol-1-yl)methyl]oxetane.

a)

1,2-Oxo-4-(2,4-dichlorophenyl)-5-(1H-1,2,4-triazol-1-yl)-4-pentanol 4-(2,4-Dichlorophenyl)-4-hydroxy-5-(1H-1,2,4-triazol-1-yl-1-pentane (described in EP 97,425) (7g, 0.023 mg and m-chloroperbenzoic acid (6.1 g, 0.035 mole) were stirred in $H_2CCl_2$ (150 mL) at room temperature for overnight. The mixture was diluted with $H_2CCl_2$ (200 mL) and washed with 10% aq. sodium carbonate and water. The $H_2CCl_2$ solution was dried ($MgSO_4$) and the solvent was removed under reduced pressure to give the title compound of Example 72(a), as a gum (7.29 g), M/e M+ 314.

b)

1-[4-(4-Isopropylpiperazin-1-yl)phenoxy]-4-(2,4-dichlorophenyl)-5-(1H-1,2,4-triazol-1-yl)-2,4-pentane diol A solution of 4-(4-isopropylpiperazin-1-yl)-phenol (5.25 g, 0.023 mole) (described in J. Med. Chem., 26, 611, (1983)) was stirred at room temperature in dry DMSO (150 mL) and NaH (0.58 g, 0.024 mole) was added. After the solution of NaH was complete, the so-formed mixture was stirred for 30 minutes and then a solution of the title compound of Example 72(a) (7.0 g, 0.022 mole) in dry DMSO (50 mL) was added dropwise. After the addition was over, the so-formed mixture was heated at 50° C. for overnight, then cooled to room temperature. H₂CCl₂ (500 mL) was added and stirred for 10 minutes. The H₂CCl₂ extract was washed with water and dried (MgSO₄). The solvent was removed to give the crude product which was dissolved in 100 mL of H₂CCl₂ and chromatographed over a silica gel column eluting with H₂CCl₂/2% MeOH v/v containing 1 mL of conc. NH₄OH per one liter to give isomer-1 (3.2 g), and isomer-2 (2.4 g) of the title compound of Example 72(b).

Isomer-1, m.p. 131–132°, M+534

Analysis: Found - C, 58.09; H, 6.2; N, 12.92; CL, 13.35%

C₂₆H₃₃N₅Cl₂O₃ requires - C, 58.42; H, 6.22;

Isomer-2, m.p. 134°, M+534

Analysis: Found - C, 58.21; H, 6.2; N, 12.36; Cl 13.23%

C₂₆H₃₃N₅Cl₂O₃ requires - C, 58.42; H, 6.22; N, 13.10; Cl, 13.26%.

c)

1-[4-(4-Isopropylpiperazin-1-yl)-phenoxy]-4-(2,4-dichlorophenyl)-5-(1H-1,2,4-triazol-1-yl)-2-tosyl-4-pentanol Isomer-1 of Example 72(b) (1.5 g, 0.028 mole) was dissolved in pyridine and was added p-toluenesulfonyl chloride (1.2 g, 0.063 mole) thereto and the so-formed solution was stirred at room temperature overnight. Pyridine was evaporated under high vacuum to provide a crude product which was extracted with H₂CCl₂ (200 mL) and washed with water. The H₂CCl₂ extract was dried over anhydrous MgSO₄ and solvent was evaporated to give the title compound of Example 72(c) (1.8 g).

d)

(±)-trans-2-[(4-(4-Isopropyl-piperazin-1-yl)-phenoxy)-methyl]-4-(2,4-dichlorophenyl)-4-[1H-1,2,4-triazol-1-yl)methyl]oxetane The title compound of Example 72(c) (1.26 g, 0.0018 mole) was dissolved in dry THF (50 mL) and cooled to 0° C. and a solution of n-butyllithium (2.5 M, 0.75 mL 0.00087 mole) in hexane was added thereto over 5 minutes. After the addition was complete, the mixture was stirred at 0° C. for 15 min. and then at 55° C. for 2 hrs. The so-formed reaction mixture was evaporated to dryness to provide a crude product which was dissolved in H₂CCl₂ and the so-formed solution was washed with water. The H₂CCl₂ extract was dried over anhydrous MgSO₄ and the solvent evaporated to dryness. The so-formed gum was chromatographed on a silica gel column setting with CH₂Cl₂/3% MeOH (v/v) to give 1.2 g of the title compound of Example 72(d), m.p. 121° C.

Elemental analysis: C, 60.25, H, 6.03, N, 13.45, Cl, 13.84; C₂₆H₃₁N₅O₂Cl₂ requires: C, 60.41; H, 6.05; N, 13.56; Cl, 13.73%.

EXAMPLE 73

(±)-cis-2-[(4-(4-Isopropylpiperazin-1-yl)-phenoxy)methyl]-4-(2,4-dichlorophenyl)-4-[1H-1,2,4-triazol-1-yl)methyl]oxetane a)

1-[4-(4-Isopropylpiperazin-1-yl)-phenoxy]-4-(2,4-dichlorophenyl)-5-(1H-1,1,2,4-triazol-1-yl)-2-tosyl-4-pentanol Isomer-2 from Example 72(b) was treated in accordance with the procedure of Example 72(c) to give 1.85 g of the title compound of Example 73(a) which was used in the next step.

b)

(±)-cis-2-[(4-(4-Isopropyl-piperazin-1-yl)-phenoxy)methyl]-4-(2,4-dichlorophenyl)-4-[1H-1,2,4-triazol-1-yl)methyl]oxetane The title compound of Example 73(a) (2.0 g) was subjected to the procedure of Example 72(d) to give 0.88 g of the title compound of Example 73 as a solid, m.p. 155°–156° C.

Elemental Analysis: C, 60.06; H, 5.78; N, 13.35; Cl, 13.59; C₂₆H₃₁N₅O₂Cl₂ requires: C, 60.41; H, 6.05; N, 13.56; and Cl, 13.73.

WHAT IS CLAIMED IS:

1. A compound represented by the formula:

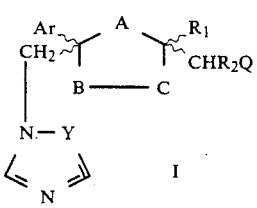

wherein:
either one of A, B or C is oxygen and the remaining two of A, B and C are CH₂, or A is oxygen, B is CH₂ and C is a direct bond;
Ar is thienyl, pyridyl, biphenyl, phenyl or phenyl substituted by one or more of halo, nitro, cyano, lower alkyl, lower alkoxy or perhalo(lower)alkyl;
Y is CH or N;

Q is 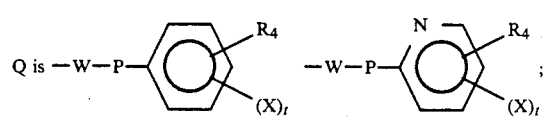

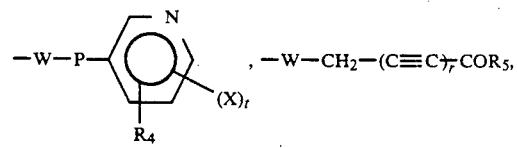

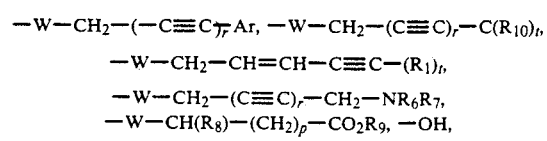

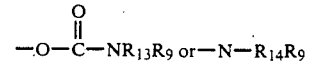

P is a direct bond, CHR₁₁ or CHR₁₁CHR₁₂;

-continued

W is $-NR_5-$, $-O-$ or $-S(O)_n-$;

X is $NO_2$, $-P-NR_6R_7$, 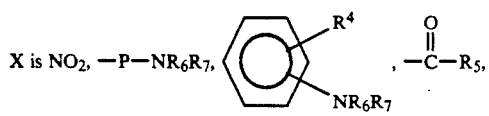 , $-C-R_5$,

AR, $OR_3$ or halogen;

$R_1$, $R_8$, $R_9$ and $R_{10}$ are independently hydrogen, lower alkyl or lower alkyl substituted by one or more hydroxyl groups;

$R_2$, $R_4$, $R_{11}$, $R_{12}$ and $R_{14}$ are hydrogen, hydroxyl, lower alkyl or lower alkyl substituted by one or more hydroxyl groups;

$R_3$ and $R_{13}$ are independently hydrogen, lower alkyl, ($C_2$-$C_8$)perhalo alkanoyl or ($C_2$-$C_8$)alkanoyl;

$R_6$ and $R_7$ are independently hydrogen, lower alkyl, phenyl or phenyl substituted by one or more of halo, perhalo(lower)alkyl, ($C_2$-$C_8$)alkanoyl, lower alkyl, lower alkyl substituted by one or more hydroxy groups, lower alkoxy, or 2-(lower)alkyl-3-oxo-1,2,4-triazol-4-yl, or $R_6$ and $R_7$ taken together with the nitrogen atom in $NR_6R_7$ form unsubstituted or substituted five or six member heterocyclyl ring systems containing carbon and one to four heteroatoms chosen from N, O and S, said heterocyclyl substituents being ($C_1$-$C_8$)alkanoyl, lower alkyl, lower alkoxycarbonyl, aminocarbonyl, N-lower alkylaminocarbonyl, N,N-di(lower alkyl)aminocarbonyl, aminothiocarbonyl, N-lower alkylaminothiocarbonyl, N,N-di(lower alkyl)aminothiocarbonyl, lower alkyl sulfonyl, phenyl-substituted lower alkyl sulfonyl, N-lower alkyl-amino, N,N-di(lower alkyl)amino, 1,3-imidazol-1-yl, 2-lower alkyl loweralkylsulfenyl-1,3-imidazol-1-yl, 2-pyridinyl, 2-thiazolyl, 2-lower alkyl-3-oxo-1,2,4-triazol-4-yl, 1-lower alkylbenzimidazol-2-yl, or phenyl or phenyl substituted by one or more of halo, perhalo lower alkyl, ($C_2$-$C_8$)alkanoyl, lower alkyl, lower alkyl substituted by one or more hydroxy groups, lower alkoxy, 1H,2,4-triazol-1-yl or 2-lower alkyl-3-oxo-1,2,4-triazol-4-yl;

$R_5$ is a lower alkyl, lower alkoxy, amino, N,N-dilower alkylamino, phenyl or phenyl substituted by one or more of halo, perhalo lower alkyl, lower alkoxy, nitro, cyano, ($C_2$-$C_8$)alkanoyl;

p is 0, 1, 2, 3, 4 or 5;
n is 0, 1 or 2;
r is 1 or 2; and
t is 0, 1, 2 or 3; and the stereochemical isomers thereof in racemic or optically active form; or a pharmaceutically acceptable salt thereof, with the proviso that when $R_2$ or $R_{11}$ or $R_{12}$ is attached to a carbon atom adjacent to $-NR_5$, $-S(O)-_n$ or $-O-$, $R_2$ or $R_{11}$ or $R_{12}$ is not hydroxyl.

2. The compound of claim 1 wherein one of A, B or C is oxygen and the remaining two of A, B and C are $CH_2$.

3. The compound of claim 1 wherein A is oxygen, B is $CH_2$ and C is a direct body.

4. A compound of claim 1 further characterized by Q being

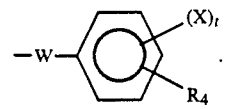

5. A compound of claim 1 above further characterized by X being $NR_6R_7$.

6. A compound of claim 5 further characterized by $NR_6R_7$ being

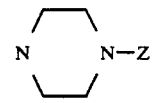

or wherein Z is hydrogen, ($C_1$-$C_8$)alkanoyl, lower alkoxycarbonyl, aminocarbonyl, N-lower alkylaminocarbonyl, N,N-di(lower alkyl)amino carbonyl, thiocarbonyl, N-loweralkylaminothiocarbonyl, N,N-di(loweralkyl)aminothiocarbonyl, lower alkyl sulfonyl, phenyl substituted lower alkyl sulfonyl, N-loweralkyl amino, N,N-di(lower alkyl)amino, 1,3-imidazol-1-yl, 2-loweralkyl-methylsulfenyl-1,3-imidazol-1-yl, 2-pyridinyl, 2-thiazolyl, 2-lower loweralkyl-3-oxo-1,2,4-triazol-4-yl, 1-lower alkylbenzimidazol-2-yl.

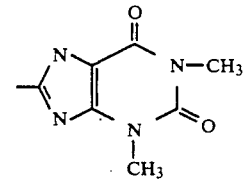

or phenyl or phenyl substituted by one or more of halo, perhalo lower alkyl, ($C_2$-$C_8$) alkanoyl, lower alkyl, lower alkyl substituted by one or more hydroxyl groups, lower alkoxy, perhalo lower alkyl, phenyl or phenyl substituted by one or more cyano, nitro, halo, perhalo lower alkyl, lower alkoxy, lower alkyl or 2-loweralkyl-3-oxo-1,2,4-triazol-4-yl or 1H,2,4-triazol-1-yl.

7. A compound of claim 1 further characterized by Q being $-S(O)_n-CH(R_8)-(CH_2)-CO_2R_9$;

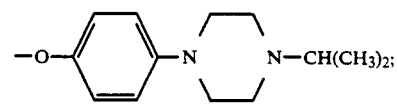

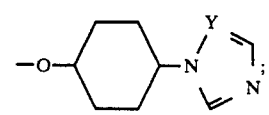

$W-CH_2-(C\equiv C)_r-C(R_1)_t$; or
$W-CH_2-C\equiv C-C\equiv C-C(CH_3)_3$.

8. A compound of claim 1 represented by the formula

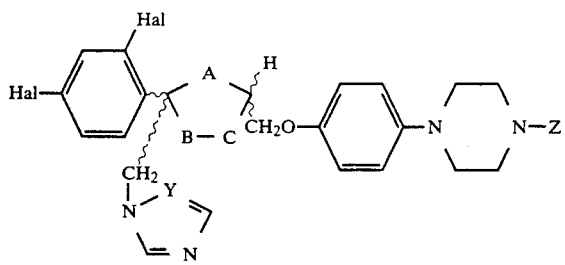

wherein:
one of A, B and C is oxygen and the remaining two of A, B and C are —CH$_2$—;
Hal is Cl or F;
Z is lower alkyl, (C$_2$-C$_8$)alkonoyl, or phenyl substituted by 2-loweralkyl-3-oxo-1,2,4triazol-4-yl.

9. A compound of the formula

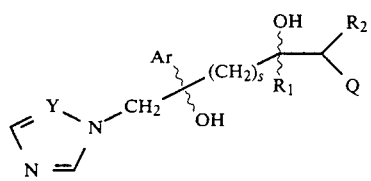

wherein Ar, R$_1$, R$_2$, Q and y are defined as in claim 1 and s is 1 or 2.

10. A pharmaceutical composition which comprises a therapeutically effective amount of a compound of claim 1 and a pharmaceutically acceptable carrier.

11. A method of treating or preventing susceptible fungal infections, hyperproliferative skin disease and/or immunological diseases including bone marrow rejection, organ transplant rejection and skin graft rejection phenomena which comprises administering to a host in need of such treating or preventing an effective amount of a compound of claim 1 in combination with a pharmaceutically acceptable carrier.

12. A compound represented by the formula:

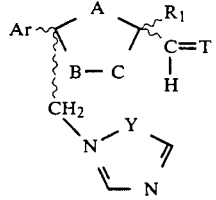

II wherein Ar is thienyl, pyridyl, biphenyl, phenyl or phenyl substituted by one or more of halo, nitro, cyano, lower alkyl, lower alkoxy or perhalo lower alkyl;
Y is CH or N;
one of A, B or C is - Oxygen and the remaining two of A, B or C are —CH$_2$—;
T is O, NOR$_1$, NNR$_1$R$_2$ or

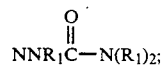

R$_1$ is hydrogen, lower alkyl or lower alkyl substituted by one or more hydroxyl groups; and R$_2$ is hydrogen, hydroxyl, lower alkyl or lower alkyl substituted by one or more hydroxyl groups.

* * * * *